(12) United States Patent
Yamamoto

(10) Patent No.: US 11,110,211 B2
(45) Date of Patent: Sep. 7, 2021

(54) PLATELET SEPARATOR, PLATELET RECOVERY DEVICE, PLATELET COLLECTION SYSTEM, AND PLATELET COLLECTION METHOD

(71) Applicant: TERUMO KABUSHIKI KAISHA, Tokyo (JP)

(72) Inventor: Hiroshi Yamamoto, Shizuoka (JP)

(73) Assignee: Terumo Kabushiki Kaisha, Tokyo (JP)

( * ) Notice: Subject to any disclaimer, the term of this patent is extended or adjusted under 35 U.S.C. 154(b) by 342 days.

(21) Appl. No.: 16/332,757

(22) PCT Filed: Sep. 15, 2017

(86) PCT No.: PCT/JP2017/033377
§ 371 (c)(1),
(2) Date: Mar. 12, 2019

(87) PCT Pub. No.: WO2018/052102
PCT Pub. Date: Mar. 22, 2018

(65) Prior Publication Data
US 2020/0222600 A1 Jul. 16, 2020

(30) Foreign Application Priority Data
Sep. 15, 2016 (JP) .............................. JP2016-180179

(51) Int. Cl.
*A61M 1/02* (2006.01)
*A61M 1/36* (2006.01)
*A61M 1/38* (2006.01)

(52) U.S. Cl.
CPC .......... *A61M 1/025* (2013.01); *A61M 1/0272* (2013.01); *A61M 1/3692* (2014.02);
(Continued)

(58) Field of Classification Search
CPC .. A61M 1/025; A61M 1/3692; A61M 1/3696; A61M 1/0272; A61M 1/382; A61M 2202/0427; A61M 2205/10
See application file for complete search history.

(56) References Cited

U.S. PATENT DOCUMENTS

| 4,834,890 A | 5/1989 | Brown et al. |
| 2011/0152055 A1 | 6/2011 | Pittinger et al. |

(Continued)

FOREIGN PATENT DOCUMENTS

| EP | 1531883 B1 | 10/2011 |
| WO | 2012060848 A1 | 5/2012 |

*Primary Examiner* — Benjamin L Lebron
(74) *Attorney, Agent, or Firm* — Terumo BCT Inc, IP Law Dept

(57) ABSTRACT

A washed platelet having a sufficiently low blood plasma content rate is more securely and efficiently obtained.
A tertiary separator (42) includes a main body (58) which has a third chamber (52) and is formed as an accommodating portion (54a) accommodating a centrifuged platelet (104), an inlet (77c) which allows a platelet containing component (100) and a platelet added solution (102) to flow in, and an outlet (78a) which allows blood plasma, the platelet added solution (102), and the platelet (104) to flow out. A bottom portion (first bottom portion (60)) of at least a portion forming the accommodating portion (54a) in a wall portion included in the main body (58) is formed of a soft material.

13 Claims, 14 Drawing Sheets

(52) U.S. Cl.
CPC .......... *A61M 1/3696* (2014.02); *A61M 1/382* (2013.01); *A61M 2202/0427* (2013.01); *A61M 2205/10* (2013.01)

(56) References Cited

U.S. PATENT DOCUMENTS

2014/0037750 A1 2/2014 Radwanski et al.
2014/0357465 A1* 12/2014 Barry, Jr. ............ A61M 1/3496
494/16

* cited by examiner

PLATELET SEPARATOR, PLATELET RECOVERY DEVICE, PLATELET COLLECTION SYSTEM, AND PLATELET COLLECTION METHOD

TECHNICAL FIELD

The present invention relates to a platelet separator, a platelet recovery device, a platelet collection system, and a platelet collection method used when a platelet is collected from blood by centrifugation.

BACKGROUND ART

At the time of transfusion of platelet preparation, there is a possibility that a patient may have a side effect from the transfusion. Blood plasma contained in the platelet preparation is considered as a cause of the side effect. For this reason, a platelet having low blood plasma content (washed platelet: also referred to as washed platelet concentrate) is desired at a transfusion site.

Patent Literature 1 discloses a blood apheresis system for collecting a platelet by centrifuging whole blood taken out of a donor. The system disclosed in Patent Literature 1 has a configuration in which a washed platelet is obtained by letting a platelet added solution flow into a chamber simultaneously with a platelet containing component at the time of centrifugation.

CITATION LIST

Patent Literature

Patent Literature 1: JP 2013-514863 A

SUMMARY OF INVENTION

Technical Problem

The invention has been conceived in connection with the above-described technology of collecting a platelet, and an object of the invention is to provide a platelet separator, a platelet recovery device, a platelet collection system, and a platelet collection method capable of more securely and efficiently obtaining a washed platelet having a sufficiently low blood plasma content rate.

Solution to Problem

In order to achieve the object, a platelet separator according to the invention includes: a main body including a chamber accommodating a platelet containing component, the main body being configured as a container capable of separating the platelet containing component into a platelet and another component in the chamber by application of a centrifugal force, at least a part of the chamber being formed as an accommodating portion that accommodates the centrifuged platelet; an inlet configured to allow the platelet containing component to flow into the chamber and configured to allow a platelet added solution to flow into the chamber; and an outlet configured to allow the other centrifuged component to flow out from the chamber and configured to allow the platelet added solution and the platelet to flow out from the chamber. A bottom portion of at least a portion forming the accommodating portion in a wall portion included in the main body is formed of a soft material.

According to the platelet separator having the above-described configuration, when the accommodating portion is included in the chamber, it is possible to accommodate the platelet centrifuged from the platelet containing component while allowing another similarly centrifuged component to flow out from the outlet. In this instance, when the platelet added solution is supplied to the chamber, another component is smoothly guided to the outlet and discharged. In this way, it is possible to securely and efficiently recover the washed platelet having a low blood plasma content rate. Further, the generated washed platelet may be expected to reduce a side effect of a transfusion. In addition, a bottom portion of at least a portion forming the accommodating portion in a wall portion included in the main body is formed of a soft material. For this reason, when an external force (for example, vibration, impact, and kneading) is supplied to the soft bottom portion during centrifugation treatment, the platelet appropriately flows in the accommodating portion, and thus sticking of the platelet to the bottom portion is suppressed, and the platelet is inhibited from being pelletized. Alternatively, when an external force is supplied to the soft bottom portion after the centrifugation treatment, it is possible to peel off the pelletized platelet from an inner surface of the main body, and to recover the peeled platelet. Therefore, it is possible to recover platelets at a high recovery rate.

In the above-described platelet separator, the whole main body may be formed of a soft material.

According to this configuration, the platelet may be inhibited from being pelletized when an external force is supplied during the centrifugation treatment, and the pelletized platelet may be peeled off when an external force is supplied after the centrifugation treatment. In particular, since the entire main body is formed of the soft material, when the external force is supplied after the centrifugation treatment, the pelletized platelet may be easily peeled off from the inner surface of the main body by largely deforming the main body.

In the above-described platelet separator, the bottom portion may be curved to bulge toward a centrifugal force direction side or an anti-centrifugal direction side.

According to this configuration, since the bottom portion is more easily deformed at the time of supplying the external force, it is possible to more effectively inhibit the platelet from being pelletized and peel off the pelletized platelet.

In the above-described platelet separator, the bottom portion may be formed to have a surface in a direction substantially orthogonal to a centrifugal force direction.

In the above-described platelet separator, the main body may include a first region and a second region having bottom portions whose heights are different from each other in the centrifugal force direction, and the bottom portion of the first region may be the bottom portion formed of the soft material and may be located at a position farther from a centrifugal center than the bottom portion of the second region.

According to this configuration, it is possible to securely store the centrifuged platelet in the first region, and to allow another component to favorably flow out from the chamber.

Furthermore, the present invention is a platelet recovery device including: a primary separation unit that accommodates whole blood collected from a donor to centrifuge the whole blood into a first blood component containing a lot of platelets and a remaining component; a secondary separation unit that accommodates the first blood component transferred from the primary separation unit to centrifuge the first blood component into a platelet containing component and a second blood component; and a tertiary separation unit that centrifuges the platelet containing component transferred from the secondary separation unit, wherein the tertiary separation unit includes a main body including a chamber accommodating the platelet containing component, the main body being configured as a container capable of separating the platelet containing component into a platelet and another component in the chamber by application of a centrifugal force, at least a part of the chamber being formed as an accommodating portion that accommodates the centrifuged platelet, an inlet configured to allow the platelet containing component to flow into the chamber and configured to allow a platelet added solution to flow into the chamber, and an outlet configured to allow the other centrifuged component to flow out from the chamber and configured to allow the platelet added solution and the platelet to flow out from the chamber, and a bottom portion of at least a portion forming the accommodating portion in a wall portion included in the main body is formed of a soft material.

In the above-described platelet recovery device, the whole main body may be formed of a soft material.

Furthermore, the present invention is a platelet collection system including: a primary separation unit that includes a first chamber accommodating whole blood collected from a donor to centrifuge the whole blood into a first blood component containing a lot of platelets and a remaining component; a secondary separation unit that includes a second chamber accommodating the first blood component transferred from the primary separation unit to centrifuge the first blood component into a platelet containing component and a second blood component; a tertiary separation unit that centrifuges the platelet containing component transferred from the secondary separation unit; and a centrifugal force application unit that applies a centrifugal force to the primary to tertiary separation units, wherein the tertiary separation unit includes a main body including a chamber accommodating the platelet containing component, the main body being configured as a container capable of separating the platelet containing component into a platelet and another component in the chamber by application of a centrifugal force, at least a part of the chamber being formed as an accommodating portion that accommodates the centrifuged platelet, an inlet configured to allow the platelet containing component to flow into the chamber and configured to allow a platelet added solution to flow into the chamber, and an outlet configured to allow the other centrifuged component to flow out from the chamber and configured to allow the platelet added solution and the platelet to flow out from the chamber, and a bottom portion of at least a portion forming the accommodating portion in a wall portion included in the main body is formed of a soft material.

In the above-described platelet collection system, the whole main body may be formed of a soft material.

In the above-described platelet collection system, the centrifugal force application unit may include an external force supply unit capable of supplying an external force to the bottom portion of the tertiary separation unit, and the platelet may be inhibited from being pelletized in the chamber by supplying the external force to the bottom portion during a centrifugation treatment of the tertiary separation unit.

According to this configuration, since the platelet maybe inhibited from being pelletized in advance in the chamber, a subsequent recovery process of the washed platelet may be efficiently performed.

In the above-described platelet collection system, the platelet added solution may be introduced into the chamber after flowing of the platelet containing component into the chamber is suspended, the other centrifuged component may be replaced with the platelet added solution in the chamber, and the platelet remaining after the replacement may be allowed to flow out together with the platelet added solution.

According to this configuration, since the platelet collection system automatically recovers the washed platelet, a recover operation by an operator may be eliminated.

Furthermore, a platelet collection method of the invention includes: a first separation process of accommodating whole blood collected from a donor in a first chamber to centrifuge the whole blood into a first blood component containing a lot of platelets and a remaining component; a first transfer process of transferring the first blood component from the first chamber to the second chamber; a second separation process of centrifuging the first blood component transferred to the second chamber into a platelet containing component and a second blood component; a second transfer process of transferring the platelet containing component to a third chamber formed in a main body of a platelet separator from the second chamber; a third separation process of centrifuging the platelet containing component transferred to the third chamber into a platelet and another component, and storing the platelet in an accommodating portion formed at least in a part of the third chamber; a replacement process of introducing a platelet added solution to the third chamber to replace the other component with the platelet added solution; and a collection process of collecting the platelet remaining in the third chamber together with the platelet added solution. A bottom portion of at least a portion forming the accommodating portion in a wall portion included in the main body is formed of a soft material.

In the above-described platelet collection method, the platelet may be inhibited from being pelletized in the third chamber when an external force supply unit provided in a centrifugal force application unit supplies an external force to the bottom portion in the third separation process.

In the above-described platelet collection method, the platelet separator may be removed from the centrifugal force application unit that applies a centrifugal force to the first to third chambers, and the platelet pelletized in the third chamber is peeled off from an inner surface of the main body by supplying an external force to the bottom portion in the collection process.

Advantageous Effects of Invention

A platelet separator, a platelet recovery device, a platelet collection system, and a platelet collection method according to the invention may more securely and efficiently obtain a washed platelet having a sufficiently low blood plasma content rate.

DESCRIPTION OF EMBODIMENTS

Hereinafter, suitable embodiments of the invention will be described in detail with reference to accompanying drawings.

Figure 1:
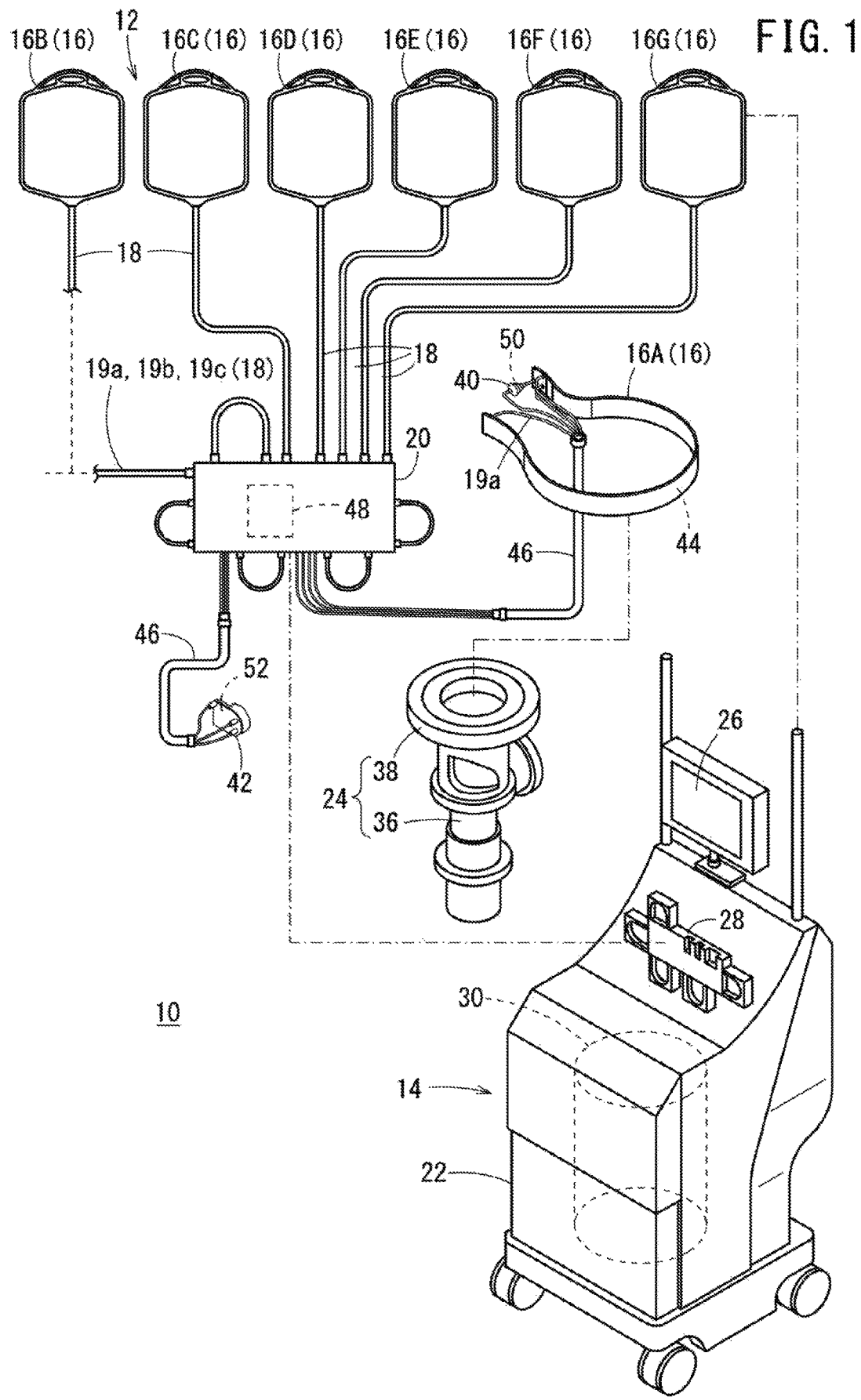
FIG. 1 is an explanatory diagram illustrating an overall configuration of a collection system according to an embodiment of the invention.

A collection system described below is configured as a blood apheresis system that centrifuges blood of a donor (a blood donor, a patient, and the like) outside a body to collect a platelet corresponding to a blood component in the blood. Hereinafter, a description will be given of the collection system for continuously taking out whole blood from the donor, performing centrifugation and returning a part of the blood component to the donor. As illustrated in FIG. 1, a platelet collection system 10 (hereafter abbreviated to "collection system 10") includes a blood collection circuit set 12 (platelet recovery device) for storing and letting a blood component flow, and a centrifugal separator 14 (centrifugal force application unit) for applying a centrifugal force to the blood collection circuit set 12.

The blood collection circuit set 12 is disposed after being used once for the sake of contamination prevention and hygiene. The blood collection circuit set 12 includes a plurality of bags 16, a plurality of tubes 18 connected to the bags 16, and a cassette 20 formed in a predetermined path to hold or connect the plurality of tubes 18. Each configuration of the blood collection circuit set 12 will be described below.

Meanwhile, the centrifugal separator 14 is a device that is repeatedly used for component collection and is provided in a medical facility, a bloodmobile, and the like. The centrifugal separator 14 includes a box-shaped main device body 22 formed relatively long in a height direction, and a rotor 24 rotatably accommodated in the main device body 22.

The main device body 22 has a function of accommodating the respective bags 16 of the blood collection circuit set 12 inside or holding the bags 16 outside and controlling centrifugation of blood taken into the blood collection circuit set 12. The main device body 22 includes a display operation device 26 for performing operation or display at the time of performing centrifugation of blood, a mounting portion 28 for mounting the cassette 20 of the blood collection circuit set 12, and an accommodating space 30 for accommodating the rotor 24.

The mounting portion 28 of the main device body 22 is formed in a frame shape on an upper side of the main device body 22, and is configured to fit and hold the cassette 20 inside. Further, the mounting portion 28 includes a plurality of pumps 32 and a plurality of clamps 34 illustrated in FIG. 2 at predetermined positions and includes a plurality of sensors (not illustrated). As the cassette 20 is mounted in the mounting portion 28, the pumps 32, the clamps 34, and the sensors are disposed on a path formed by the tubes 18 and the cassette 20 of the blood collection circuit set 12.

The accommodating space 30 of the main device body 22 is provided below the mounting portion 28 described above and is formed in a cylindrical shape extending along a vertical direction of the main device body 22. A rotary drive source (not illustrated) for mounting and rotating the rotor 24 is provided at a bottom of the accommodating space 30.

The rotor 24 of the centrifugal separator 14 is configured to be freely taken out from the main device body 22, so that the blood collection circuit set 12 may be easily mounted. The rotor 24 includes a shaft 36 elongated in the vertical direction and a conduit housing 38 provided in at an upper end portion of the shaft 36. In a state in which the rotor 24 is accommodated in the accommodating space 30, a lower end portion of the shaft 36 is coupled and fixed to the rotary drive source.

The conduit housing 38 is formed in an annular shape having an outer diameter larger than that of the shaft 36. A primary separation bag 16A corresponding to a first separation unit of the blood collection circuit set 12 is mounted along a circumferential direction on an outer peripheral surface of the conduit housing 38. In addition, several cavities 38a for accommodating a secondary separator 40 (secondary separation unit) and a tertiary separator 42 (tertiary separation unit, platelet separator) of the blood collection circuit set 12 are provided inside the conduit housing 38 (see FIG. 3). The conduit housing 38 rotates integrally with the shaft 36 under the control of the main device body 22.

Next, a description will be given of a connection state of the respective bags 16 and the respective tubes 18 of the blood collection circuit set 12 with reference to FIG. 2. The blood collection circuit set 12 includes the primary separation bag 16A, an ACD liquid storage bag 16B, an auxiliary bag 16C, an additive solution storage bag 16D, a PPP bag 16E, a disposal bag 16F, and a WPC bag 16G as the above-described plurality of bags 16. An ACD solution corresponding to an anticoagulant of blood is stored in the ACD liquid storage bag 16B in advance, and a platelet added solution 102 is stored in the additive solution storage bag 16D in advance. Meanwhile, the primary separation bag 16A, the auxiliary bag 16C, the PPP bag 16E, the disposal bag 16F, and the WPC bag 16G have cavities that may accommodate a fluid.

As illustrated in FIG. 1, the primary separation bag 16A is formed in a belt-shaped bag. A first chamber 44, to which whole blood of the donor is supplied, is provided in the primary separation bag 16A. The primary separation bag 16A is wound around the outer circumferential surface of the conduit housing 38 when the blood collection circuit set 12 is mounted. Alternatively, the conduit housing 38 may include a pocket (not illustrated) around an outer periphery thereof to accommodate the primary separation bag 16A. One end portion and another end portion of the primary separation bag 16A are connected by a connecting body (a string, or the like) (not illustrated) when the conduit housing 38 is mounted.

An introduction tube 19a is connected to the one end portion side of the primary separation bag 16A. The introduction tube 19a is held by the cassette 20 by passing through the inside of a bundle tube 46 illustrated in FIG. 1, is exposed to the outside through a predetermined path in the cassette 20, and is connected to a blood inlet/outlet (not illustrated) of the donor. For example, the blood inlet/outlet includes an indwelling needle, and the like inserted and indwelled in a blood vessel of the donor. A pump 32a for sucking blood from the blood inlet/outlet is provided at a midway position of the introduction tube 19a. In addition, a supply tube 19c of the ACD liquid storage bag 16B is connected to the introduction tube 19a. A pump 32b for sucking the ACD liquid from the ACD liquid storage bag 16B is provided at a midway position of the supply tube 19c so that the collection system 10 supplies the ACD liquid to the introduction tube 19a to suppress coagulation of the whole blood.

The whole blood flowing into the first chamber 44 from the one end portion to which the introduction tube 19a is connected flows on the outer peripheral of the conduit housing 38 in the circumferential direction along the belt shape of the primary separation bag 16A toward the other end portion. Then, the whole blood receives a centrifugal force due to rotation of the rotor 24 (conduit housing 38), whereby centrifugation is performed during the flow thereof.

Figure 2:
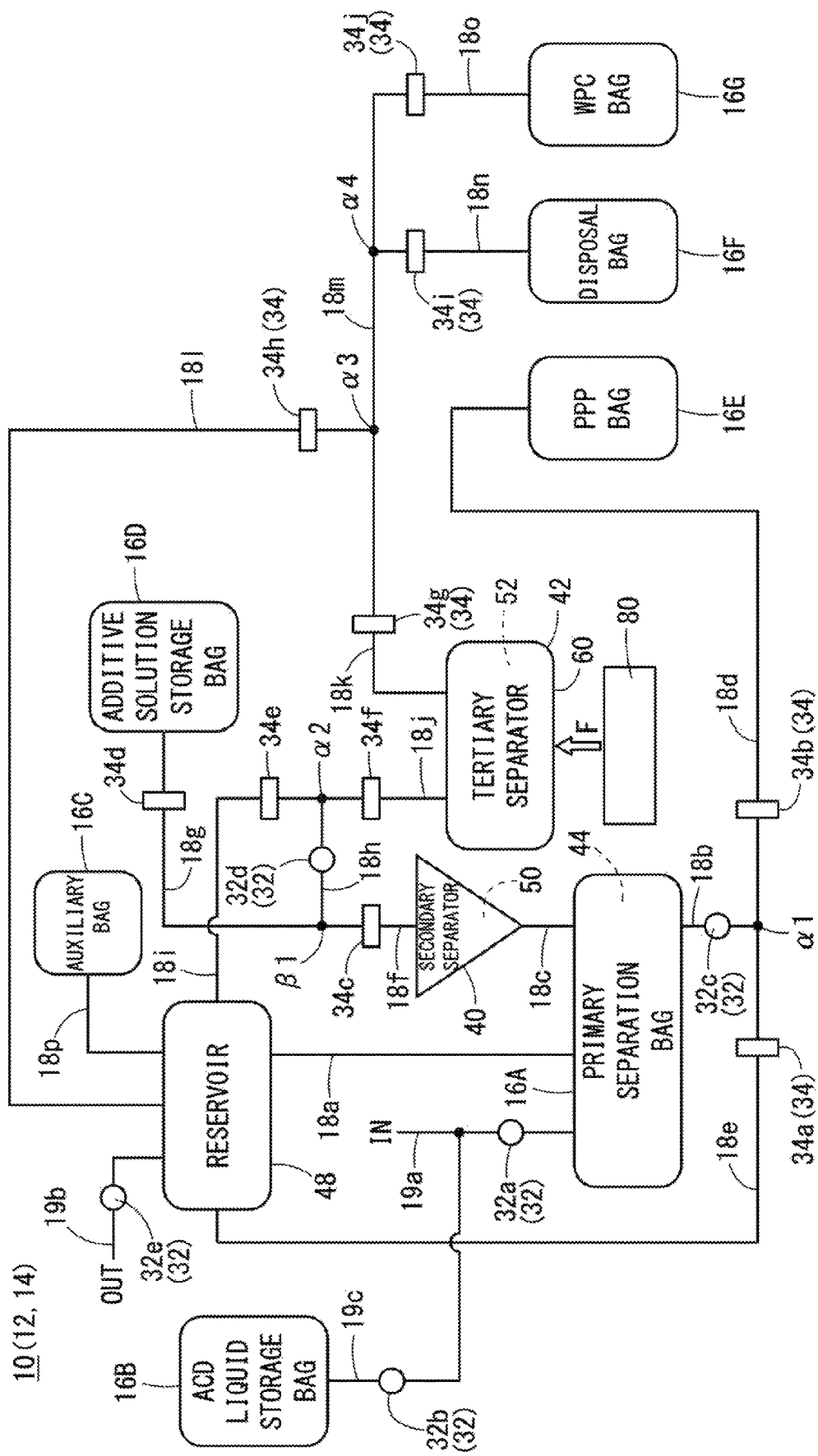
FIG. 2 is a block diagram schematically illustrating a circuit configuration example of a blood collection circuit set of FIG. 1.

As illustrated in FIGS. 1 and 2, first to third tubes 18a to 18c are connected to the other end portion side of the primary separation bag 16A. The first tube 18a is coupled to a lower side of the other end portion of the primary separation bag 16A and is connected to a reservoir 48 provided in the cassette 20 through the inside of the bundle tube 46. The first tube 18a allows concentrated red blood cells (remaining components) generated by centrifugation of the first chamber 44 to flow out to the reservoir 48.

The second tube 18b is connected to an upper side of the other end portion of the primary separation bag 16A. The second tube 18b passes through a predetermined path in the bundle tube 46 and the cassette 20 and branches into a fourth tube 18d connected to the PPP bag 16E and a fifth tube 18e connected to the reservoir 48 at a branch point α1.

A pump 32c is provided at a midway position of the second tube 18b, and the pump 32c allows a blood plasma component (platelet poor plasma) generated by centrifugation of the whole blood to flow out or flow in. A clamp 34b is provided in the fourth tube 18d, and a clamp 34a is provided in the fifth tube 18e.

The third tube 18c is connected to an intermediate portion in the vertical direction of the other end portion of the primary separation bag 16A. The end portion of the third tube 18c on the opposite side is connected to the secondary separator 40 in the conduit housing 38. The third tube 18c allows a buffy coat (first blood component) produced by centrifugation of whole blood to flow out. The buffy coat contains leukocyte component and platelet rich plasma (platelet containing component). That is, the buffy coat has a lot of platelets.

Figure 3:
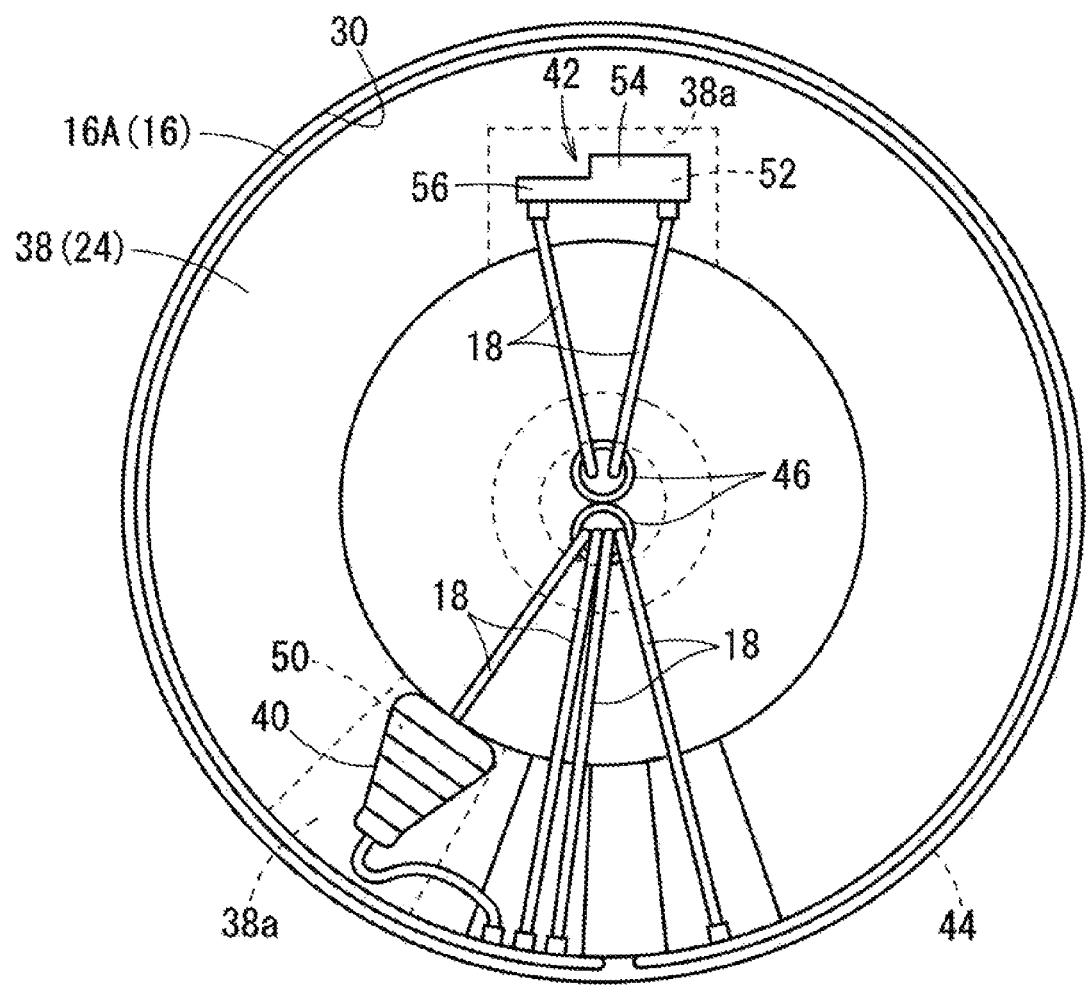
FIG. 3 is a plan view illustrating an arrangement example of a primary separation bag, a secondary separator, and a tertiary separator of the blood collection circuit set of FIG. 1.

The secondary separator 40 has a second chamber 50 for temporarily accommodating the buffy coat, and the buffy coat is further centrifuged by applying a centrifugal force from the conduit housing 38. The secondary separator 40 is formed in a conical shape. As illustrated in FIG. 3, in a mounted state of the conduit housing 38, a top portion thereof is disposed on a side far from a centrifugal center, and a bottom surface thereof is disposed on a side close to the centrifugal center.

The third tube 18c is connected to a top portion of the secondary separator 40, and a sixth tube 18f (first flow passage) is connected to a bottom surface thereof. In addition, the secondary separator 40 has a plurality of steps on a tapered side surface, so that when the buffy coat is centrifuged, the leukocyte component (second blood component) having heavy specific gravity is captured by each step, and a platelet containing component 100 (also see FIG. 8B) containing blood plasma and a platelet having light specific gravity is brought to the centrifugal center. Then, the platelet containing component 100 is allowed to flow out from the sixth tube 18f.

The sixth tube 18f is connected to the cassette 20 by passing through the bundle tube 46 from the secondary separator 40, joins a seventh tube 18g (second flow passage) at a junction β1 in the cassette 20, and is connected to an eighth tube 18h. A clamp 34c (first clamp) is provided at a midway position of the sixth tube 18f. The seventh tube 18g is connected to the additive solution storage bag 16D, and a clamp 34d (second clamp) is provided at a midway position thereof.

The eighth tube 18h extends between the junction β1 and the branch point α2, and includes a pump 32d at midway position thereof. Further, the eighth tube 18h branches into a ninth tube 18i connected to the reservoir 48 and a tenth tube 18j connected to the tertiary separator 42 at the branch point α2. In addition, a clamp 34e is provided in the ninth tube 18i, and a clamp 34f is provided in the tenth tube 18j.

An end portion of the tenth tube 18j on the opposite side from the branch point α2 is connected to an inflow port 77 of the tertiary separator 42. The tertiary separator 42 has a third chamber 52 accommodated in the conduit housing 38 to temporarily store the platelet containing component 100 flowing in from the sixth tube 18f and the platelet added solution 102 flowing in from the seventh tube 18g.

Further, the tertiary separator 42 separates the platelet containing component 100 into blood plasma (another component) and a platelet by a centrifugal force applied thereto. A configuration of the tertiary separator 42 will be described in detail below. An eleventh tube 18k extending into the cassette 20 through the bundle tube 46 is connected to the tertiary separator 42.

The eleventh tube 18k is a tube through which liquid (blood component, platelet added solution, washed platelet) flows out from the tertiary separator 42. A clamp 34g is provided in the eleventh tube 18k. The eleventh tube 18k is divided into a twelfth tube 18l connected to the reservoir 48 and a thirteenth tube 18m at a downstream branch point α3.

A clamp 34h is provided in the twelfth tube 18l. Further, the thirteenth tube 18m is divided into a fourteenth tube 18n connected to the disposal bag 16F and a fifteenth tube 18o connected to the WPC bag 16G at a branch point α4. Clamps 34i and 34j are provided in the fourteenth and fifteenth tubes 18n and 18o, respectively.

The reservoir 48 provided in the cassette 20 temporarily stores a blood component to be returned to the donor. In addition to the first, fifth, ninth and twelfth tubes 18a, 18e, 18i, and 18l, a sixteenth tube 18p connected to the auxiliary bag 16C and a lead-out tube 19b connected to the blood inlet/outlet of the donor are connected to the reservoir 48.

The introduction tube 19a, the lead-out tube 19b, and the supply tube 19c are connected to the cassette 20 as a triple tube. A pump 32e for allowing the blood component returned to the donor to flow is provided at a midway position of the lead-out tube 19b. In the present embodiment, the introduction tube 19a and the lead-out tube 19b are connected to one indwelling needle of the blood inlet/outlet so that blood collection and blood return are performed using the same needle. However, the collection system 10 may be configured to perform blood collection and blood return through separate paths using two or more needles.

The blood collection circuit set 12 is configured as described above by being attached to the centrifugal separator 14. When the centrifugal separator 14 is driven, the blood collection circuit set 12 centrifuges the whole blood of the donor by the conduit housing 38, the pump 32, and the clamp 34 operating at an appropriate timing.

Next, the configuration of the tertiary separator 42 will be described in detail. As illustrated in FIG. 3, the tertiary separator 42 is fixedly disposed in a cavity 38a formed on the inner side of the conduit housing 38. As a result, a centrifugal force weaker than a centrifugal force applied to the primary separation bag 16A and the secondary separator 40 is applied to the tertiary separator 42 as the conduit housing 38 rotates.

In the centrifugal separator 14, the tertiary separator 42 is disposed at an opposite position from both end portions of the primary separation bag 16A attached to the conduit housing 38 with the centrifugal center interposed therebetween in order to stabilize rotation of the conduit housing 38 during centrifugation. The position at which the tertiary separator 42 is disposed may be freely designed. For example, the tertiary separator 42 may be placed near a position at which the secondary separator 40 is disposed.

Figure 4:
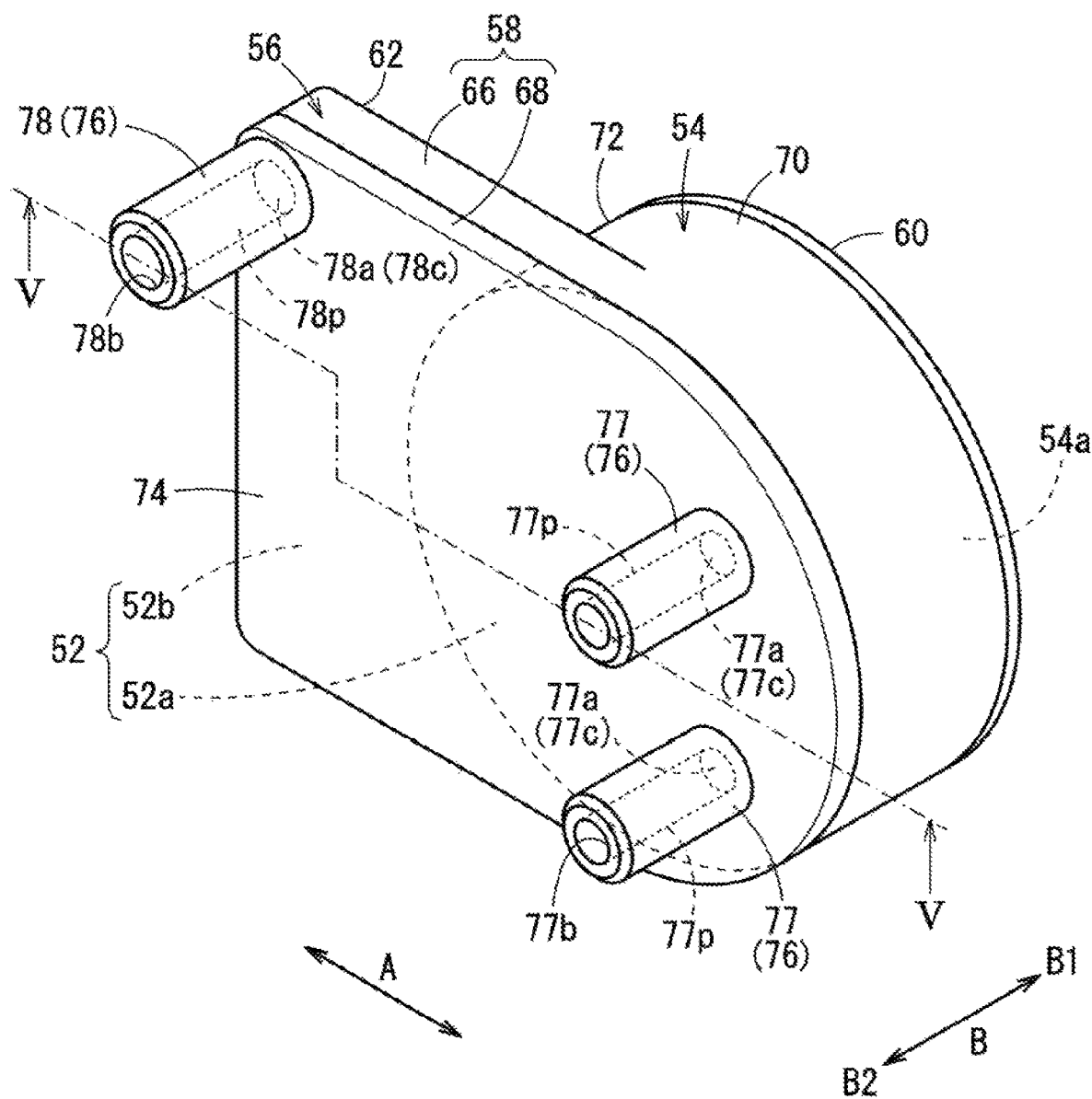
FIG. 4 is a perspective view illustrating the tertiary separator of FIG. 1.
Figure 5:
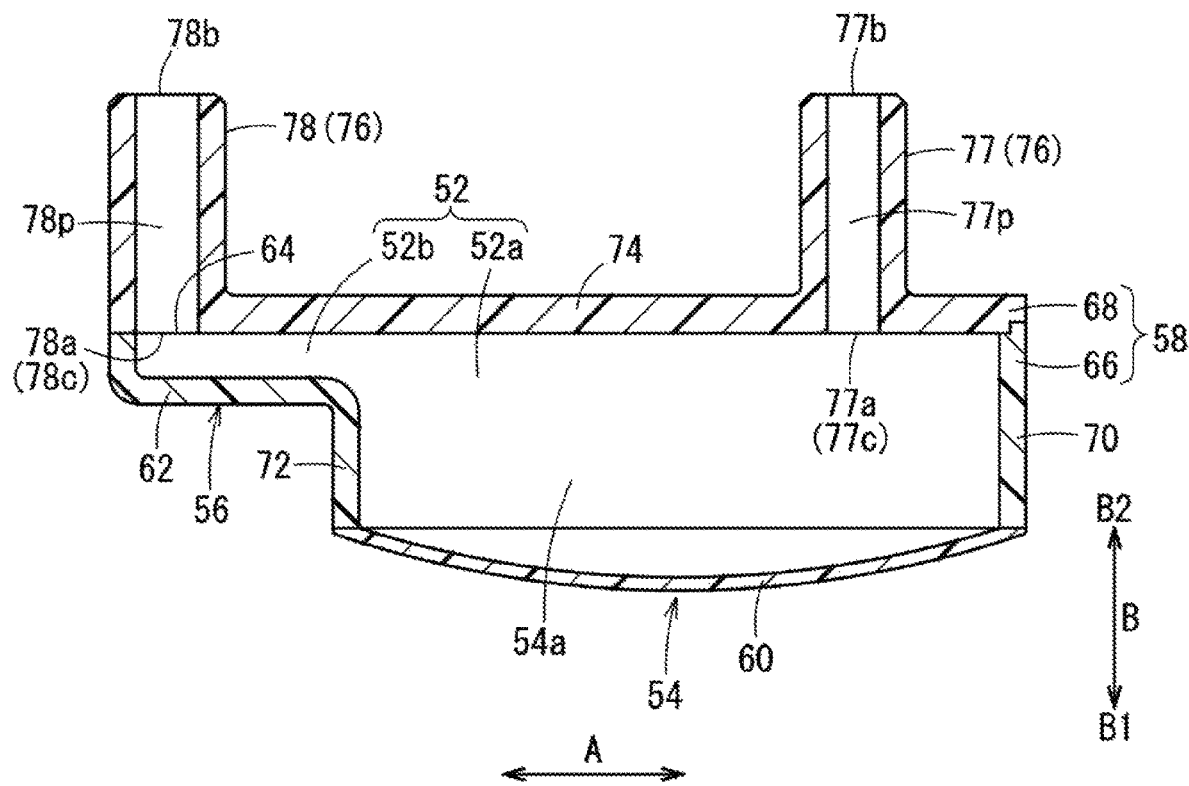
FIG. 5 is a cross-sectional view taken along line V-V of FIG. 4.
Figure 8B:
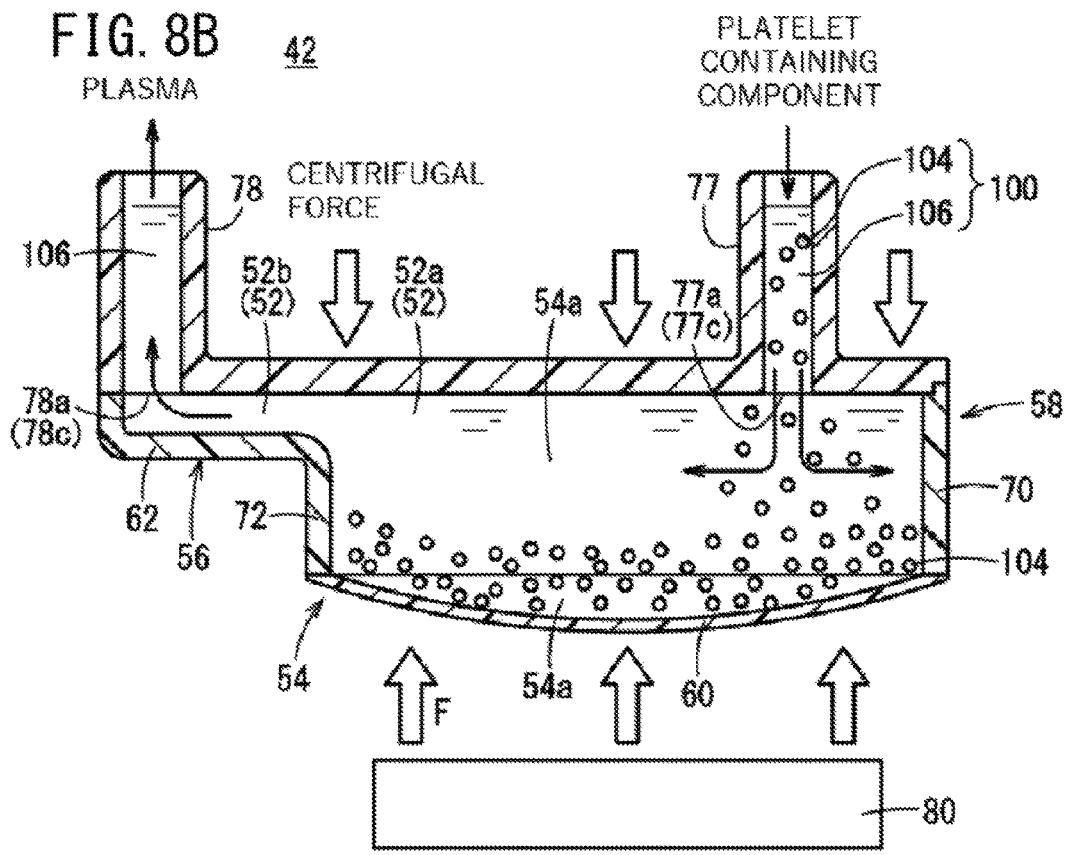
FIG. 8B is a cross-sectional view schematically illustrating a state of the tertiary separator of FIG. 8A.
Figure 9A:
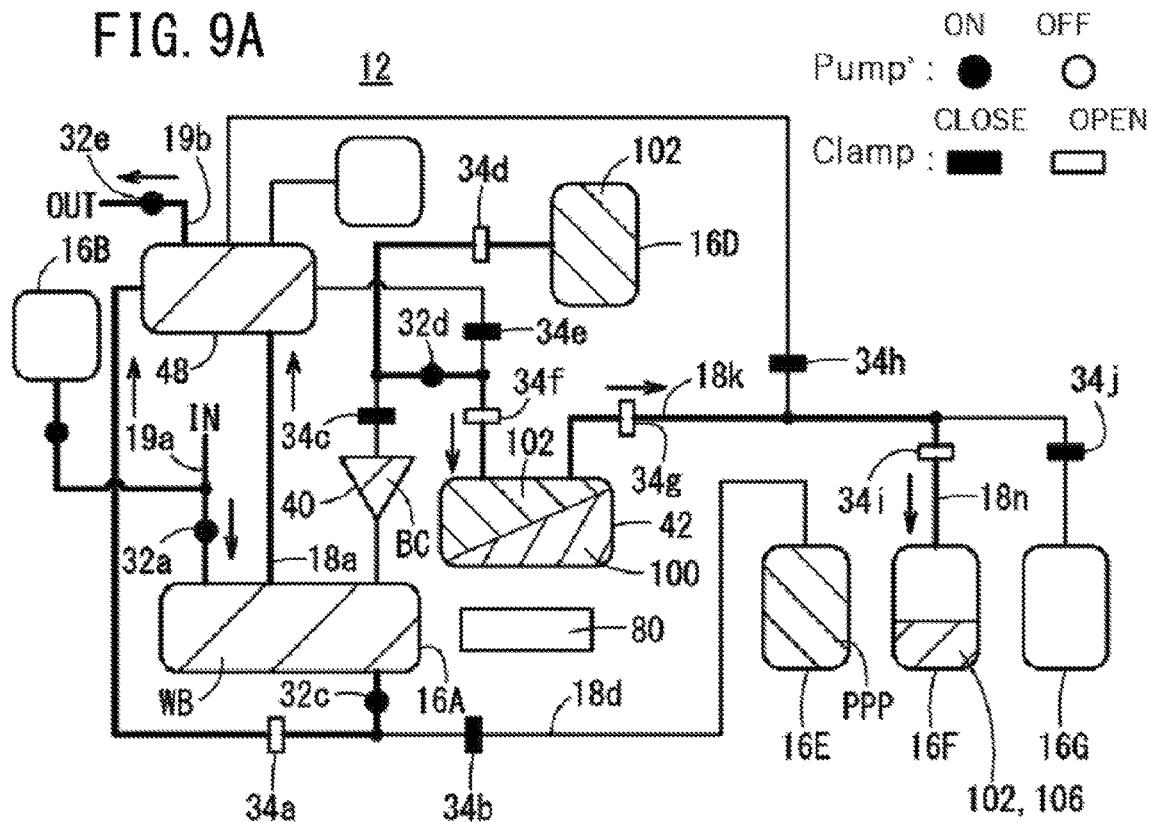
FIG. 9A is a third explanatory diagram illustrating an operation of the blood collection circuit set subsequent to FIG. 8A.
Figure 9B:
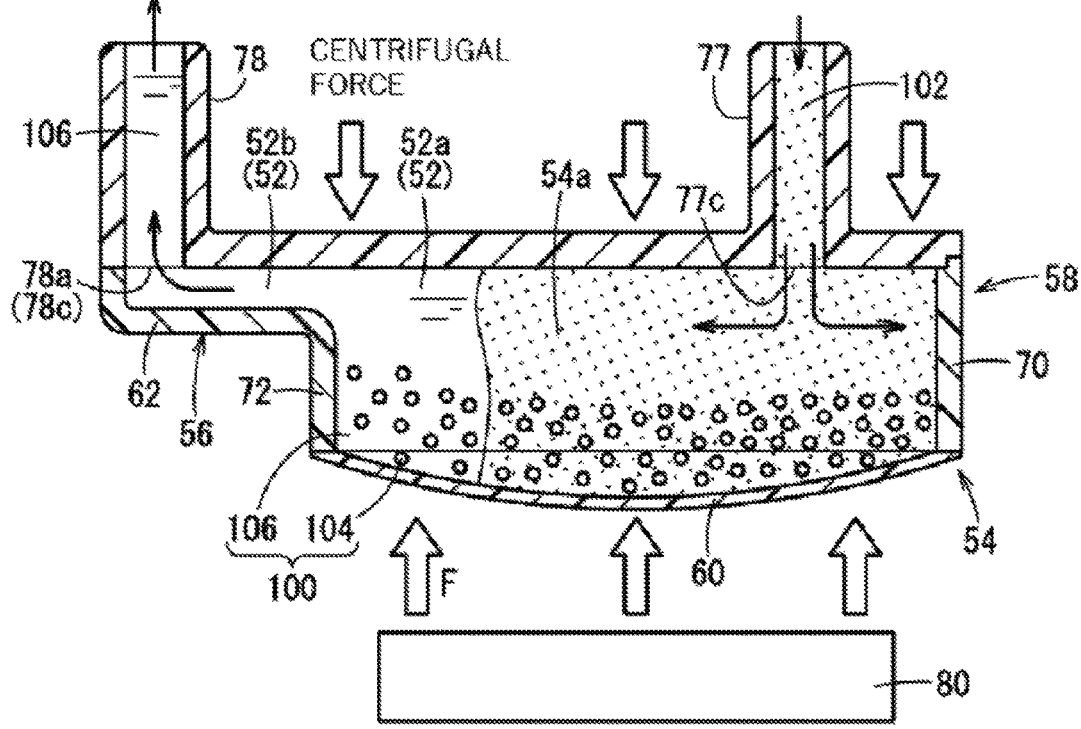
FIG. 9B is a cross-sectional view schematically illustrating a state of the tertiary separator of FIG. 9A.

As illustrated in FIGS. 4 and 5, the tertiary separator 42 includes a main body 58 in the form of a container capable of storing the platelet containing component 100 (see FIG. 8B) and the platelet added solution 102 (see FIG. 9B). The main body 58 is formed in a substantially rectangular shape in a front view as seen from the centrifugal center. Further, the main body 58 has a first region 54 which extends from a center portion in a longer direction (a direction of an arrow A) to one side and is thick in a centrifugal force direction (a direction of an arrow B1) in a plan view and a second region 56 which extends to another side in the longer direction and is thin in the centrifugal force direction in the plan view.

The first region 54 and the second region 56 have widths in a short direction set to be equal to each other, and are connected to each other. One side of the first region 54 in the longer direction is formed on a side having a rounded corner whose radius of curvature is large in a front view. The other side of the second region 56 in the longer direction is formed on a side having a rounded corner whose radius of curvature is small in the front view.

The first region 54 constructs a first space 52a having large volume on the inside by having a first bottom portion 60 a long distance away from a ceiling 74 on the centrifugal center side in a centrifugal direction. The second region 56 constructs a second space 52b having small volume on the inside by having a second bottom portion 62 a short distance away from the ceiling 74 in the centrifugal direction. In other words, the first bottom portion 60 is located at a position farther from the centrifugal center than the second bottom portion 62. The first bottom portion 60 is formed to have a surface in a direction substantially perpendicular to the centrifugal force direction. The ceiling 74 of the first region 54 and the ceiling 74 of the second region 56 are connected and flush with each other. The first space 52a and the second space 52b communicate with each other in the longer direction to form the third chamber 52. That is, the third chamber 52 has the first space 52a and the second space 52b communicating with each other.

The first bottom portion 60 (a bottom portion of at least a portion forming an accommodating portion 54a in a wall portion included in the main body 58) is formed of a soft material. A thickness of the first bottom portion 60 is thinner than a thickness of a wall portion other than the first bottom portion 60 in the main body 58. Meanwhile, the wall portion other than the first bottom portion 60 in the main body 58 is formed of a hard material (for example, hard resin). Examples of the hard resin include polypropylene, polycarbonate, and the like.

Since the first bottom portion 60 is formed of the soft material, the first bottom portion 60 is more easily deformed than another portion of the main body 58. That is, the first bottom portion 60 is a film-shaped body which is easily deformed by supplying an external force F (see FIG. 8B, and the like). Examples of a material of the first bottom portion 60 include polyvinyl chloride, polyamide, polyamide elastomer, polyurethane, and the like.

In FIG. 5, the first bottom portion 60 is curved to bulge toward a centrifugal force direction side (arrow B1 direction side). The first bottom portion 60 may be curved to bulge toward an anti-centrifugal force direction side (arrow B2 direction side), or may be formed in a flat shape.

As illustrated in FIG. 2, in the present embodiment, the centrifugal separator 14 includes an external force supply unit 80 capable of supplying an external force F to (the first bottom portion 60 of) the tertiary separator 42. Examples of the external force F include vibration, impact, kneading, and the like. Therefore, examples of the form of the external force supply unit 80 include a vibrator, a striking device, a finger pump, and the like. The external force supply unit 80 is installed in the conduit housing 38 (see FIG. 1) of the rotor 24.

In a state in which the tertiary separator 42 is attached to the conduit housing 38, the external force supply unit 80 faces or comes into contact with the tertiary separator 42. Accordingly, when the external force supply unit 80 operates in this state, the external force F is supplied to the first bottom portion 60 of the tertiary separator 42. The operation of the external force supply unit 80 is controlled by a controller of the centrifugal separator 14.

In FIG. 5, the main body 58 is configured to be separable into a container 66 having the third chamber 52 and having an opening 64 of the third chamber 52 in the opposite direction to the centrifugal force direction (anti-centrifugal force direction: the direction of the arrow B2) and a lid 68 attached to the opening 64 of the container 66.

The container 66 has the above-mentioned first and second bottom portions 60 and 62 and a side wall 70 protruding from each of the bottom portions 60 and 62 in the anti-centrifugal force direction. The side wall 70 surrounds the first and second bottom portions 60 and 62 in the circumferential direction to form the third chamber 52. In addition, since the depths (heights) of the first bottom portion 60 and the second bottom portion 62 are different from each other, the container 66 has a step wall 72 at a boundary therebetween.

In the front view, the step wall 72 has a shape in which a central portion in the vertical direction is recessed toward the second region 56 side. The first bottom portion 60, the step wall 72, and the side wall 70 from the first bottom portion 60 to a position corresponding to the same height as that of the step wall 72 form the accommodating portion 54a therein to accommodate (store) a platelet in response to centrifugation. In other words, the accommodating portion 54a is a space that is set at a portion of the first space 52a close to the first bottom portion 60 (the arrow B1 direction side).

The step wall 72 more easily stores the platelet by being formed in a wall orthogonal to the first and second bottom portions 60 and 62 in a cross-sectional view illustrated in FIG. 5. Further, it is preferable to set a height of the step wall 72 (an interval in the anti-centrifugal force direction from the first bottom portion 60 to the second bottom portion 62) to be higher than a height of a separation boundary surface when the platelet containing component 100 is centrifuged into a platelet and blood plasma. In this way, the platelet is greatly restrained from climbing over the step wall 72. Thus, blood plasma may be more securely discharged by suppressing an outflow of the platelet from the third chamber 52.

Meanwhile, the lid 68 includes the ceiling 74 which has a flat plate shape corresponding to a front shape of the side wall 70 of the container 66, and the ceiling 74 closes the opening 64 of the container 66 using an appropriate attachment means such as adhesion. A plurality of attachment ports 76 for attaching the tubes 18 (tenth and eleventh tubes 18j and 18k) (see FIG. 2) connected to the tertiary separator 42 is provided on the ceiling 74 of the lid 68.

The plurality of attachment ports 76 is formed in a cylindrical shape and extends in a direction (direction of an arrow B) orthogonal to a plane direction of the ceiling 74. A communication passage is formed through an axial center of each of the attachment ports 76 along an axial direction. Diameters of the communication passages of the respective attachment ports 76 may be set to be the same or different from each other according to a fluid scheduled to flow. The plurality of attachment ports 76 includes a pair of inflow ports 77 and an outflow port 78.

The pair of inflow ports 77 allows the platelet containing component 100 and the platelet added solution 102 to flow into the third chamber 52 when the tenth tube 18j (see FIG. 2) of the blood collection circuit set 12 is connected thereto. In other words, although not illustrated in detail in FIG. 2, the tenth tube 18j branches into two branches at a midway position from the branch point α2 to the tertiary separator 42, and this branch tube is attached to each of the pair of inflow ports 77.

The blood collection circuit set 12 may constitute various circuits besides a circuit for allowing the platelet containing component 100 and the platelet added solution 102 to flow in from the common inflow port 77 as described above. For example, the platelet containing component 100 and the platelet added solution 102 may be allowed to separately flow in by connecting the sixth tube 18f to one inflow port 77 and connecting the seventh tube 18g to the other inflow port 77. In addition, one or three or more inflow ports 77 may be provided.

As illustrated in FIG. 4, the pair of inflow ports 77 is formed at positions at one side of the first region 54 in the longer direction and spaced apart from each other in the short direction. As illustrated in FIG. 5, each of the inflow ports 77 protrudes from the ceiling 74 in the anti-centrifugal force direction (the direction of the arrow B2). An opening 77a communicating with a communication passage 77p of the inflow port 77 is formed in the ceiling 74. Therefore, in the tertiary separator 42, two openings 77a constitute inlets 77c allowing a liquid (the platelet containing component 100 and the platelet added solution 102) to flow into the third chamber 52.

When one or three or more inflow ports 77 are provided, the inlets 77c may include one or three or more openings 77a. The inlets 77c are open to the first space 52a (accommodating portion 54a) in the plan view. The inlets 77c are open at positions facing the first bottom portion 60.

An opening 77b for allowing the fluid in the tenth tube 18j to flow into the communication passage 77p is provided at a protruding end of each of the inflow ports 77 protruding in the anti-centrifugal direction.

The outflow port 78 is connected to the eleventh tube 18k (see FIG. 2) of the blood collection circuit set 12, and mainly allows the blood plasma 106, the platelet added solution 102 and a washed platelet 108 to flow out from the third chamber 52. The outflow port 78 is provided at a position close to an upper corner portion of the second region 56 in the front view. The outflow port 78 protrudes in the anti-centrifugal direction from the ceiling 74. An opening 78a communicating with a communication passage 78p of the outflow port 78 is provided on a surface of the ceiling 74 opposite to a formation position of the outflow port 78. The opening 78a constitutes an outlet 78c that allows a fluid (the blood plasma 106, the platelet added solution 102 and the washed platelet 108) to flow out from the third chamber 52 (the second space 52b). The outlet 78c opens at a position facing the second bottom portion 62 of the second region 56. An opening position of the outlet 78c is not limited to the illustrated position, and may be any position at which the outlet 78c is open to the second space 52b.

The outlet 78c is not limited to a configuration including one opening 78a, and may include two or more openings 78a. An opening 78b for allowing the fluid in the communication passage 78p to flow out into the eleventh tube 18k is provided at a protruding end of the outflow port 78 in the anti-centrifugal force direction.

The tertiary separator 42 is not limited to the above configuration, and may adopt various application examples and modifications. For example, the tertiary separator 42 may be provided with two or more outflow ports 78, or the inflow port 77 or the outflow port 78 may be provided in the container 66.

Further, for example, the tertiary separator 42 may not include the first bottom portion 60 and the second bottom portion 62 having different heights, and may include a flat bottom portion (accommodating portion 54a) sufficiently spaced from the opening 78a of the outflow port 78 in the centrifugal direction. That is, the tertiary separator 42 may centrifuge the platelet and the blood plasma in the third chamber 52 to allow the blood plasma to flow out, and a shape thereof or a position of the opening of the port is not particularly limited. The second bottom portion 62 may not be formed in a flat shape in a plan sectional view, and may be formed in a concave shape, a convex shape, and the like.

Basically, the collection system 10 according to the present embodiment is configured as described above, and a function and effect thereof will be described below.

At the time of preparing the collection system 10, a medical staff such as a doctor or a nurse attaches the blood collection circuit set 12, in which the tube 18 is suitably wired to the cassette 20, to the centrifugal separator 14. In this instance, the medical staff wraps the primary separation bag 16A around the outer peripheral surface of the conduit housing 38, and accommodates the rotor 24 in the accommodating space 30 of the centrifugal separator 14. Further, the cassette 20 is mounted in the mounting portion 28 of the centrifugal separator 14, and the other bags 16B to 16G are hung on a stand, and the like (not illustrated). In response to the cassette 20 being mounted, the clamps 34, the pumps 32 and the sensors are disposed at predetermined positions of the tube 18.

Figure 6:
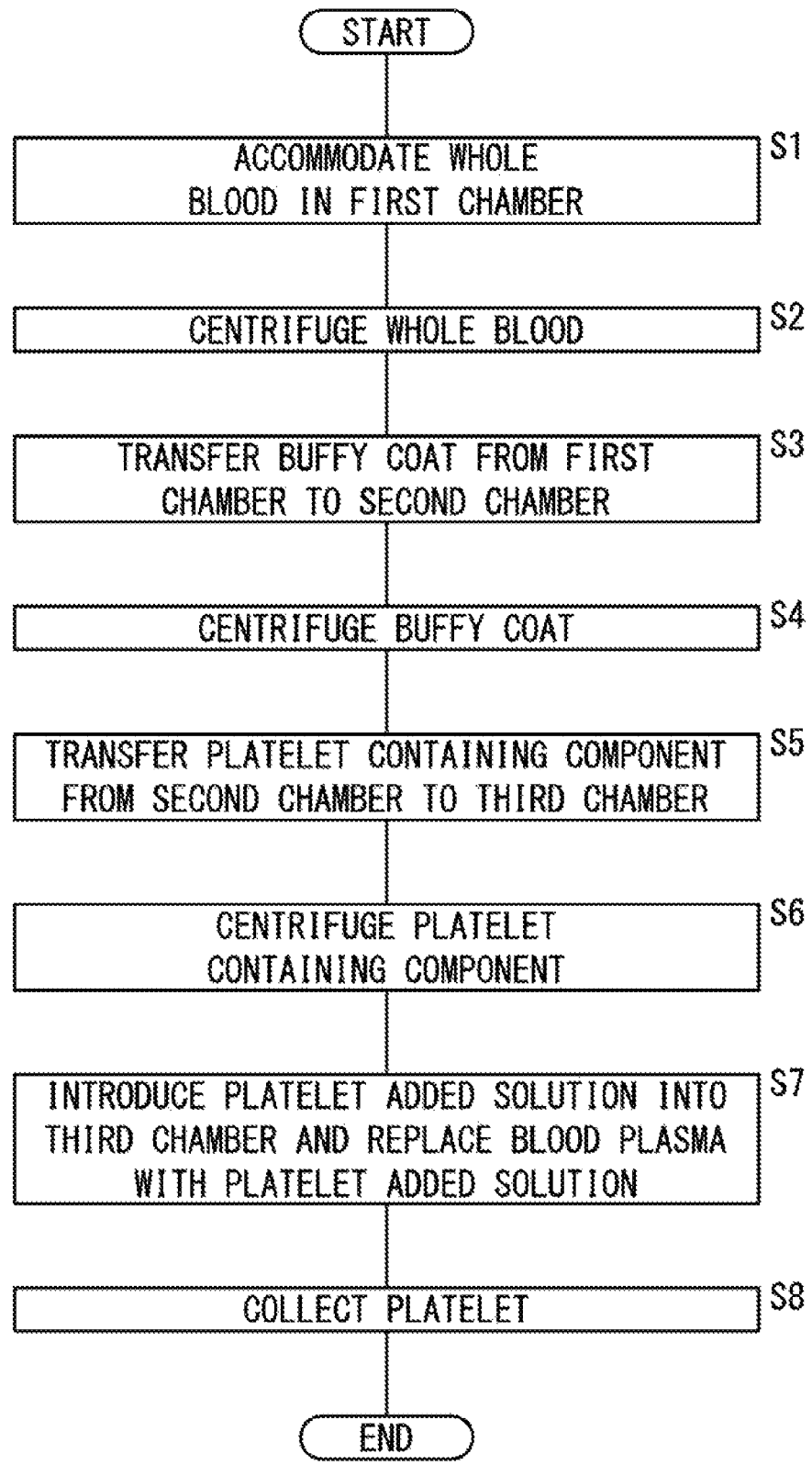
FIG. 6 is a flowchart of a method of collecting a platelet according to the collection system of FIG. 1.

In component collection, first, the medical staff pierces the donor with the indwelling needle, and connects connectors of the introduction tube 19a and the lead-out tube 19b of the blood collection circuit set 12 to the indwelling needle to construct the blood inlet/outlet. Then, the operation of the collection system 10 is started. Under the control of the controller (not illustrated) provided in the centrifugal separator 14, the collection system 10 collects a platelet by extracorporeally treating the blood component according to a procedure of a flowchart illustrated in FIG. 6.

In this case, the collection system 10 accommodates the whole blood of the donor in the first chamber 44 of the primary separation bag 16A (step S1), and centrifuges the whole blood by rotating the primary separation bag 16A (step S2). Subsequently, the buffy coat separated by centrifugation of whole blood is transferred from the first chamber 44 to the second chamber 50 of the secondary separator 40 (step S3), and the buffy coat is centrifuged by rotating the secondary separator 40 (step S4). Subsequently, the platelet containing component 100 separated by centrifugation of the buffy coat is transferred from the second chamber 50 to the third chamber 52 of the tertiary separator 42 (step S5), and the platelet containing component 100 is centrifuged by rotating the tertiary separator 42 (step S6). Further, the platelet added solution 102 is introduced into the third chamber 52, and the blood plasma separated by centrifugation of the platelet containing component 100 is replaced with the platelet added solution 102 (step S7). Then, the platelet remaining in the third chamber 52 is collected together with the platelet added solution 102 (step S8). Hereinafter, a method of collecting the platelet will be described in more detail.

Figure 7:
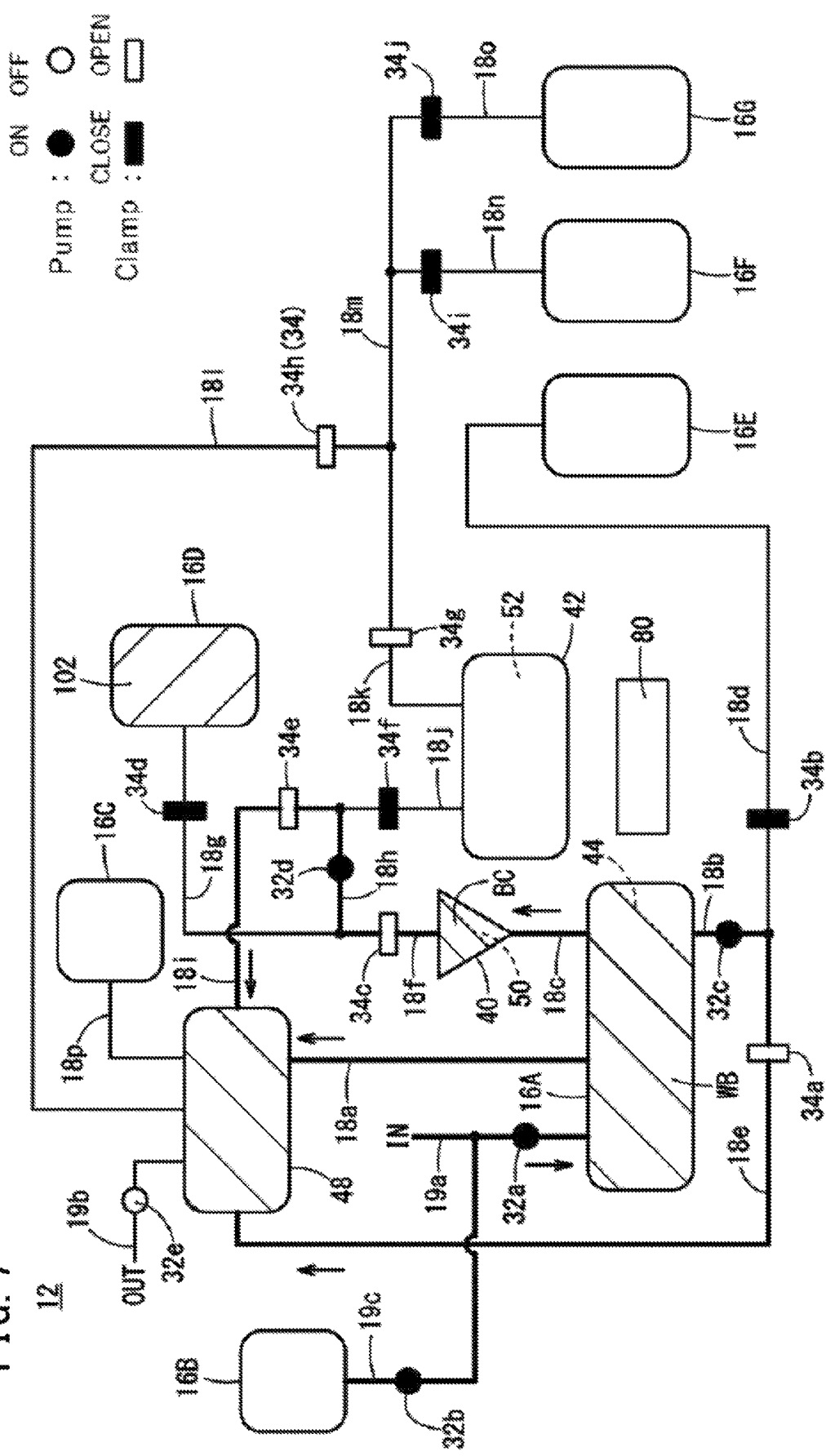
FIG. 7 is a first explanatory diagram illustrating an operation of the blood collection circuit set at the time of collecting a blood component.

As illustrated in FIG. 7, in step S1, the collection system 10 drives the pump 32a of the introduction tube 19a to suck whole blood WB from the blood inlet/outlet formed in the donor, and allows the whole blood WB to flow into the first chamber 44 of the primary separation bag 16A. For example, a flow velocity of the whole blood WB is preferably in a range of 60 to 120 mL/min. In this instance, the ACD liquid is supplied from the ACID liquid storage bag 16B by driving the pump 32b to suppress coagulation of the whole blood WB. The whole blood WB is continuously supplied to the first chamber 44 and flows from one end side of the belt shape to which the introduction tube 19a is connected toward the other end side (also see FIG. 1).

During this flow, the centrifugal separator 14 performs step S2. That is, the rotor 24 is rotated at a predetermined rotational speed to apply a centrifugal force to the primary separation bag 16A. In this way, when the whole blood WB flows to the other end side, the whole blood WB is separated into the concentrated red blood cells, the platelet poor plasma, and the buffy coat BC according to the specific gravities of the components.

In step S3, the centrifugal separator 14 drives the pump 32d to allow the buffy coat BC to flow to the secondary separator 40 through the third tube 18c. In addition, the centrifugal separator 14 allows the concentrated red blood cells to flow to the reservoir 48 through the first tube 18a. Further, the centrifugal separator 14 allows the platelet poor plasma to flow to the reservoir 48 through the second and fifth tubes 18b and 18e by driving the pump 32c, opening the clamp 34a, and closing the clamp 34b.

The secondary separator 40 performs step S4 when a centrifugal force is applied thereto in response to rotation of the conduit housing 38. That is, in the second chamber 50, the buffy coat BC is centrifuged into a white blood cell and the platelet containing component 100. Then, the centrifugal separator 14 opens the clamps 34c and 34e and closes the clamps 34d and 34f, thereby allowing the platelet containing component 100 to temporarily flow to the reservoir 48.

Figure 8A:
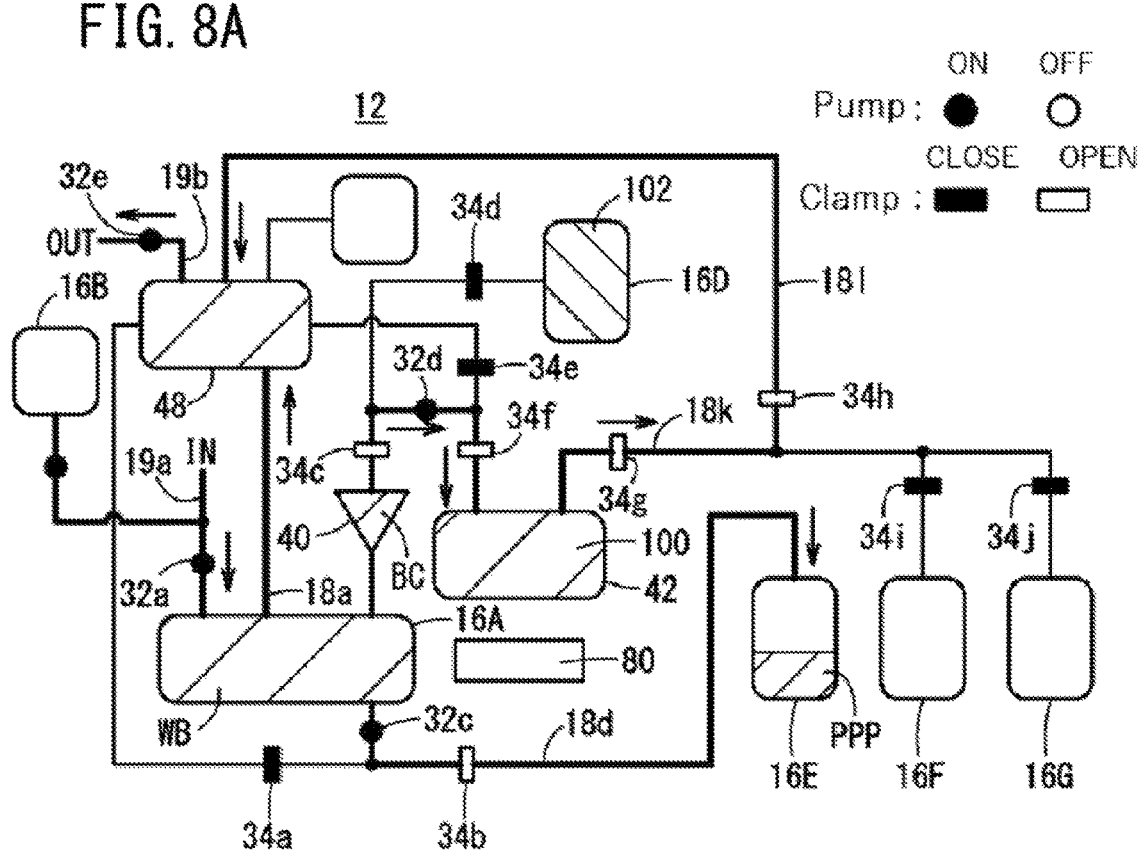
FIG. 8A is a second explanatory diagram illustrating an operation of the blood collection circuit set subsequent to FIG. 7.

Thereafter, the centrifugal separator 14 performs step S5. That is, as illustrated in FIG. 8A, the centrifugal separator 14 closes the clamp 34e and opens the clamp 34f, thereby allowing the platelet containing component 100 to flow from the secondary separator 40 to the tertiary separator 92. In this instance, since the clamp 34d is closed, a flow of the platelet added solution 102 is regulated. In addition, the centrifugal separator 14 closes the clamp 34a and opens the clamp 34b, thereby storing the platelet poor plasma in the PPP bag 16E.

In response to start of step S5, the platelet containing component 100 flows into the tertiary separator 42 through the sixth, eighth and tenth tubes 18f, 18h, 18j (see FIG. 8B). When a plurality of openings 77a of the inflow port 77 is provided in the main body 58, the platelet containing component 100 is allowed to uniformly flow without being concentrated in one place.

Then, the centrifugal separator 14 performs step S6 corresponding to a platelet separation process when a centrifugal force is applied thereto in response to rotation of the conduit housing 38. That is, the platelet containing component 100 is centrifuged into the platelet 104 and the blood plasma 106 in the first space 52a of the third chamber 52. In this instance, the platelet 104 moves in the centrifugal force direction with respect to the blood plasma 106 (that is, to the accommodating portion 54a of the first space 52a). Further, the platelet 104 is inhibited from moving to the second space 52b side by the step wall 72. On the other hand, the blood plasma 106 gathers in the anti-centrifugal force direction, and easily flows from the first space 52a to the second space 52b in response to continuous inflow of the platelet containing component 100. Then, the blood plasma 106 passes through the outlet 78c and flows out to the outside of the tertiary separator 42 through the outflow port 78. For this reason, the platelet 104 gradually accumulates and concentrates in the accommodating portion 54a.

During execution of the platelet separation process (step S6), the external force supply unit 80 supplies the external force F to the first bottom portion 60 of the tertiary separator 42. Due to the supply of the external force F, the first bottom portion 60 moves with deformation. Due to the movement of the first bottom portion 60, the platelet 104 is not completely precipitated on the first bottom portion 60 and flows in the accommodating portion 54a. For this reason, sticking of the platelet 104 to the first bottom portion 60 is suppressed, and the platelet 104 is inhibited from being pelletized. The platelet 104 does not rise to a position higher than the second bottom portion 62 by operation of the first bottom portion 60 accompanying the supply of the external force F. In other words, strength of the external force F is set such that the platelet 109 does not flow to a position higher than the second bottom portion 62.

As illustrated in FIG. 8A, the centrifugal separator 14 guides the blood plasma 106 flowing out from the outflow port 78 to the reservoir 48 by opening the clamps 34g and 34h. The blood components (the concentrated red blood cells, the blood plasma, and the like) stored in the reservoir 48 flows and are returned to the blood inlet/outlet of the donor through the lead-out tube 19b by driving the pump 32e. Then, the centrifugal separator 14 maintains a state illustrated in FIG. 8A and FIG. 8B (that is, continues execution of steps S1 to S6) until sufficient platelet poor plasma is stored in the PPP bag 16E. When the storing in the PPP bag 16E is completed, the clamp 34b is closed and the clamp 34a is opened to allow the platelet poor plasma to flow to the reservoir 48 (see FIG. 9A).

After the platelet 104 is concentrated in the third chamber 52, the centrifugal separator 14 closes the clamps 34c and 34e and opens the clamps 34d and 34f as illustrated in FIG. 9A. In this way, the centrifugal separator 14 supplies the platelet added solution 102 to the tertiary separator 42.

In other words, the centrifugal separator 14 performs step S7 corresponding to a replacement process to allow the platelet added solution 102 to flow into the third chamber 52 from the inflow port 77 as illustrated in FIG. 9B. The platelet added solution 102 moves in the anti-centrifugal force direction in response to receiving a centrifugal force from the conduit housing 38 when the platelet added solution 102 has smaller specific gravity than that of the platelet 104. Then, when the platelet added solution 102 is continuously supplied from the inflow port 77, the platelet added solution 102 flows to the outflow port 78 side while pushing out the blood plasma 106 in the third chamber 52, and is discharged from the tertiary separator 42. Therefore, in the third chamber 52, the blood plasma 106 is replaced with the platelet added solution 102 while the platelet 104 remains.

As illustrated in FIG. 9B, the external force supply unit 80 supplies the external force F to the first bottom portion 60 of the tertiary separator 42 even during execution of the replacement process (step S7). In this way, sticking of the platelet 104 to the first bottom portion 60 is suppressed, and the platelet 104 is inhibited from being pelletized in the accommodating portion 54a as much as possible. In this case, the strength of the external force F is set such that the platelet 104 does not flow to a position higher than the second bottom portion 62.

Returning to FIG. 9A, in response to supply of the platelet added solution 102 to the tertiary separator 42, the centrifugal separator 14 closes the clamp 34h and opens the clamp 34i. In this way, the blood plasma 106 and the platelet added solution 102 flows to the disposal bag 16F, and the platelet added solution 102 is prevented from flowing into the donor through the reservoir 48 and the blood inlet/outlet.

Figure 10A:
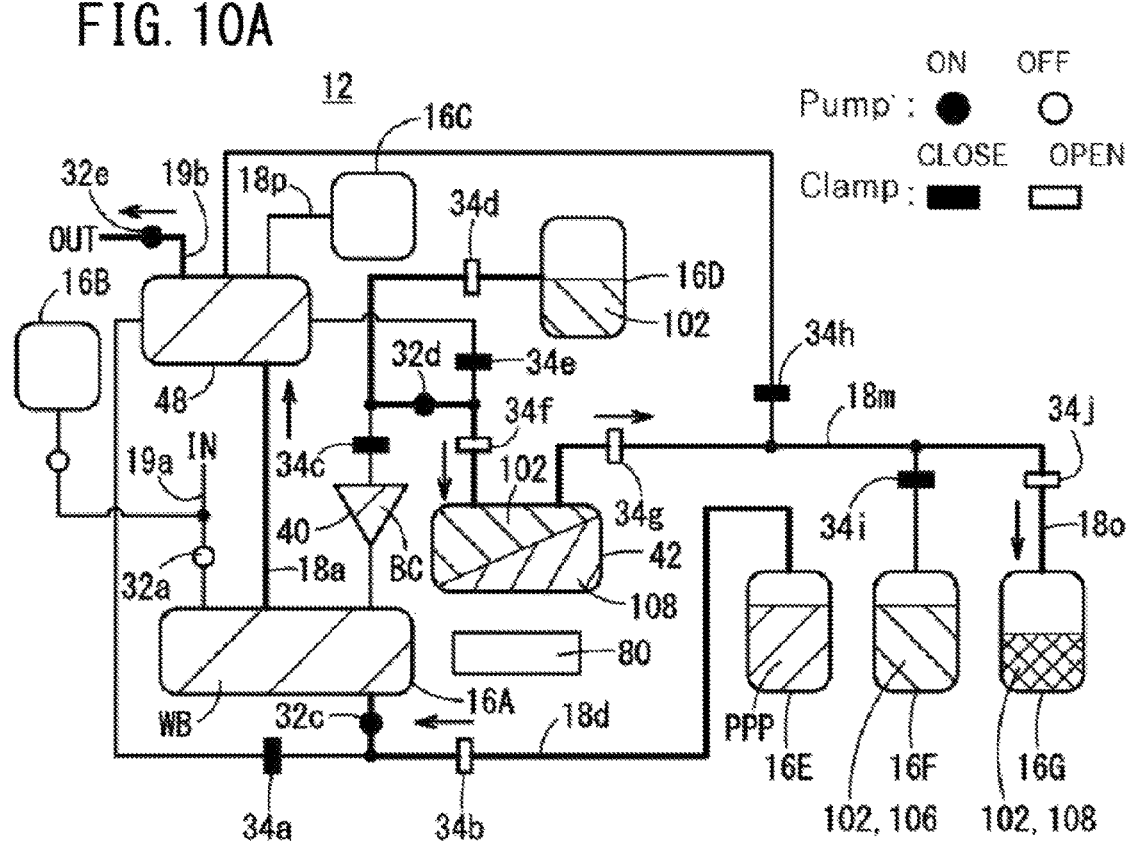
FIG. 10A is a fourth explanatory diagram illustrating an operation of the blood collection circuit set subsequent to FIG. 9A.

After continuing the state illustrated in FIGS. 9A and 9B to some extent, the centrifugal separator 14 returns a part of the platelet poor plasma taken in the PPP bag 16E to the primary separation bag 16A by driving the pump 32c as illustrated in FIG. 10A. Then, the platelet poor plasma is allowed to flow to the reservoir 48 from the primary separation bag 16A, thereby returning these blood components to the donor through the lead-out tube 19b.

Thereafter, application of the centrifugal force to the primary separation bag 16A, the secondary separator 40, and the tertiary separator 42 is suspended by stopping the rotation of the rotor 24. Then, in order to perform step S8 corresponding to a platelet collection process, the centrifugal separator 14 raises a flow rate (introduction rate) of the platelet added solution 102 above that in the replacement process (step S7) by driving the pump 32d to vigorously supply the platelet added solution 102 to the third chamber 52. For example, the introduction rate of the platelet added solution 102 is about 5 mL/min in the replacement process (step S7), and is set to about 100 mL/min in the platelet collection process (step S8).

Figure 10B:
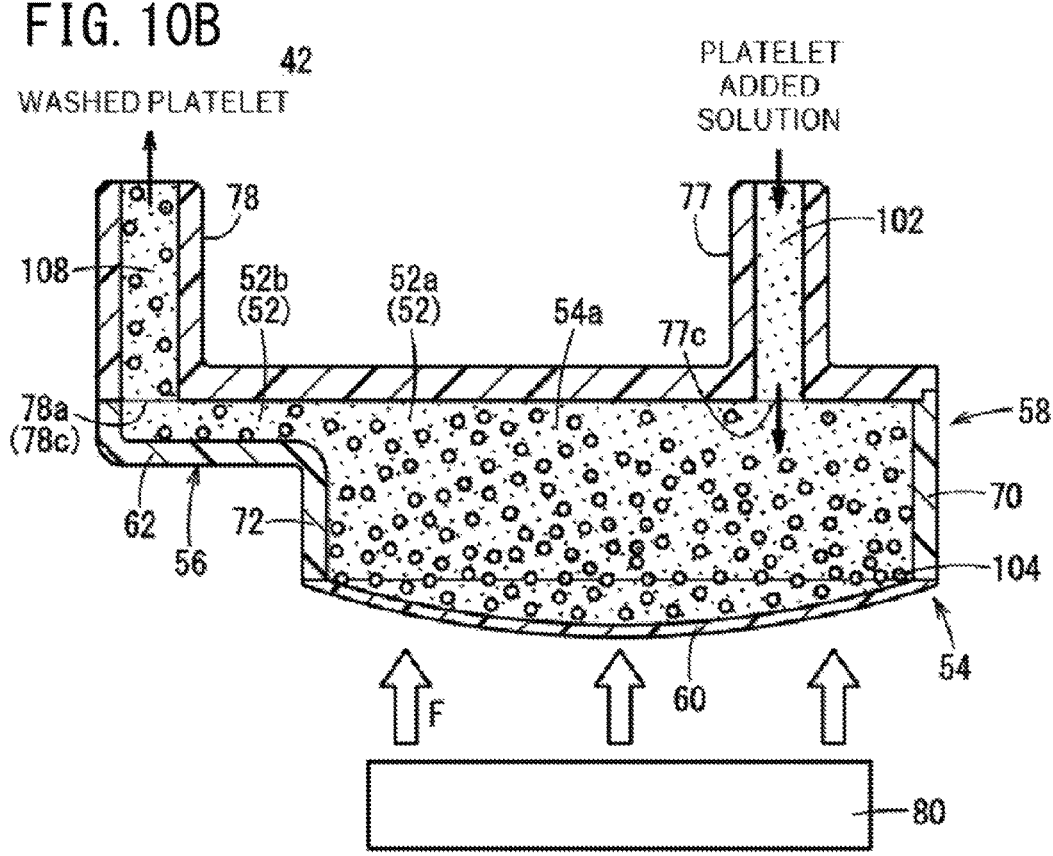
FIG. 10B is a cross-sectional view schematically illustrating a state of the tertiary separator of FIG. 10A.

In this way, as illustrated in FIG. 10B, the platelet added solution 102 allows the washed platelet 108 mixed with the platelet 104 and the platelet added solution 102 to flow out from the outflow port 78. That is, when the platelet added solution 102 having an increased flow rate is introduced into the third chamber 52, the platelet 104 is agitated by a strong flow of the platelet added solution 102. Therefore, the platelet 104 moves on a flow of the platelet added solution 102 which rises to an anti-centrifugal force direction side (a position higher than the second bottom portion 62) in the third chamber 52 and is directed to the outlet 78c.

In this way, the platelet 104 is discharged as the washed platelet 108 from the outflow port 78 together with the platelet added solution 102. When the blood plasma 106 is replaced with the platelet added solution 102, a blood plasma content rate of the washed platelet 108 is 5% or less. As illustrated in FIG. 10B, in the platelet collection process (step S8), the external force supply unit 80 may supply the external force F to the first bottom portion 60 of the tertiary separator 42. In this way, the platelet 104 may be rapidly raised to an upper side in the third chamber 52, and the platelet 104 may be more efficiently recovered.

As illustrated in FIG. 10A, when the clamps 34h and 34i are closed and the clamps 34g and 34j are opened, the washed platelet 108 is stored in the WPC bag 16G. Further, when a target amount of the washed platelet 108 is stored in the WPC bag 16G, the clamp 34j is closed, and collection of the washed platelet 108 is completed.

As described above, according to the collection system 10 according to the present embodiment, the washed platelet 108 is obtained by centrifuging the platelet containing component 100 transferred to the third chamber 52 to the platelet 104 and the blood plasma 106 and replacing the blood plasma 106 with the platelet added solution 102. In this way, it is possible to easily remove the blood plasma 106 from the platelet containing component 100 to more securely and efficiently obtain the washed platelet 108 having a sufficiently low blood plasma content rate. Further, the generated washed platelet 108 may be expected to reduce a side effect of a transfusion.

In this case, at the time of collecting the platelet 104, when a different centrifugal force from that of the first and second chambers 44 and 50 is applied in centrifugation of the third chamber 52, the platelet containing component 100 may be satisfactorily separated into the platelet 104 and the blood plasma 106. In addition, when the first chamber 44 and the second chamber 50 communicate with each other and the second chamber 50 and the third chamber 52 communicate with each other, a blood component freely flows, and a circuit for collecting the platelet 104 from the whole blood WB is constructed in a simple and hygienic manner. Furthermore, when the white blood cell is separated in the second chamber 50, it is possible to inhibit the white blood cell from being mixed with the platelet containing component 100 supplied into the third chamber 52, and to obtain the washed platelet 108 containing few white blood cells.

In addition, during centrifugation, the third chamber 52 of the collection system 10 may allow the blood plasma 106 to flow out while introducing the platelet containing component 100 to continuously centrifuge the platelet containing component 100, thereby concentrating the platelet 104 in the third chamber 52. In addition, when a flow destination of the blood plasma 106 centrifuged in the third chamber 52 is selectively changed, the blood plasma 106 may be favorably returned by preventing the platelet added solution 102 from flowing into the donor. Further, when the platelet added solution 102 is allowed to flow in from the seventh tube 18g unlike the platelet containing component 100, the platelet added solution 102 may be allowed to smoothly flow into the third chamber 52, and replacement with the platelet added solution 102 may be rapidly and stably performed.

Further, in the method of collecting the platelet 104 and the collection system 10, the separated blood plasma 106 is smoothly replaced with the platelet added solution 102 when only the platelet added solution 102 flows in at the time of introducing the platelet added solution 102. In this instance, the collection system 10 may easily switch between supply of the platelet containing component 100 to the third chamber 52 and supply of the platelet added solution 102 by switching between opening and closing of the clamps 34c and 34d. Furthermore, at the time of collecting the platelet 104, it is possible to recover the platelet 104 as the washed platelet 108 by increasing the introduction rate of the platelet added solution 102.

In the present embodiment, when the accommodating portion 54a is included in the third chamber 52, it is possible to accommodate the platelet 104 centrifuged from the platelet containing component 100 while allowing another similarly centrifuged component to flow out from the outlet 78c. In this instance, when the platelet added solution 102 is supplied to the chamber, another component is smoothly guided to the outlet 78c and discharged. In this way, it is possible to securely and efficiently recover the washed platelet 108 having a low blood plasma content rate. Further, the generated washed platelet 108 may be expected to reduce a side effect of a transfusion.

Further, the first bottom portion 60 (a bottom portion of at least a portion forming the accommodating portion 54a in the wall portion included in the main body 58) is formed of a soft material. For this reason, when the external force F (for example, vibration, impact, and kneading) is supplied to the soft first bottom portion 60 during centrifugation treatment, the platelet 104 appropriately flows in the accommodating portion 54a, and thus sticking of the platelet 104 to the first bottom portion 60 is suppressed, and the platelet 104 is inhibited from being pelletized.

In the present embodiment, the first bottom portion 60 is curved to bulge toward the centrifugal force direction side or the anti-centrifugal direction side. For this reason, the first bottom portion 60 is more easily deformed when the external force is supplied, and thus the platelet 104 may be more effectively inhibited from being pelletized.

In the present embodiment, the main body 58 includes the first region 54 and the second region 56 having bottom portions whose heights are different from each other in the centrifugal force direction. The bottom portion of the first region 54 (first bottom portion 60) is located at a position farther from the centrifugal center than the bottom portion of the second region 56 (the second bottom portion 62). For this reason, it is possible to securely store the centrifuged platelet 104 in the first region 54, and to allow other components to favorably flow out from the third chamber 52.

In the collection system 10 according to the present embodiment, the platelet 104 is prevented from being pelletized in the third chamber 52 by supplying the external force F to the first bottom portion 60 during centrifugation treatment of the tertiary separator 42. In this way, it is possible to inhibit the platelet 104 from being pelletized in the third chamber 52, and thus it is possible to efficiently perform a subsequent recovery process for recovering the washed platelet 108.

In addition, in the collection system 10 according to the present embodiment, after flowing of the platelet containing component 100 into the third chamber 52 is suspended, the platelet added solution 102 is introduced into the third chamber 52, another centrifuged component (the blood plasma 106) is replaced with the platelet added solution 102 in the third chamber 52, and the platelet 104 remaining after replacement is allowed to flow out together with the platelet added solution 102. In this way, the collection system 10 automatically recovers the washed platelet 108, and thus recovery work by an operator may not be performed.

Figure 11:
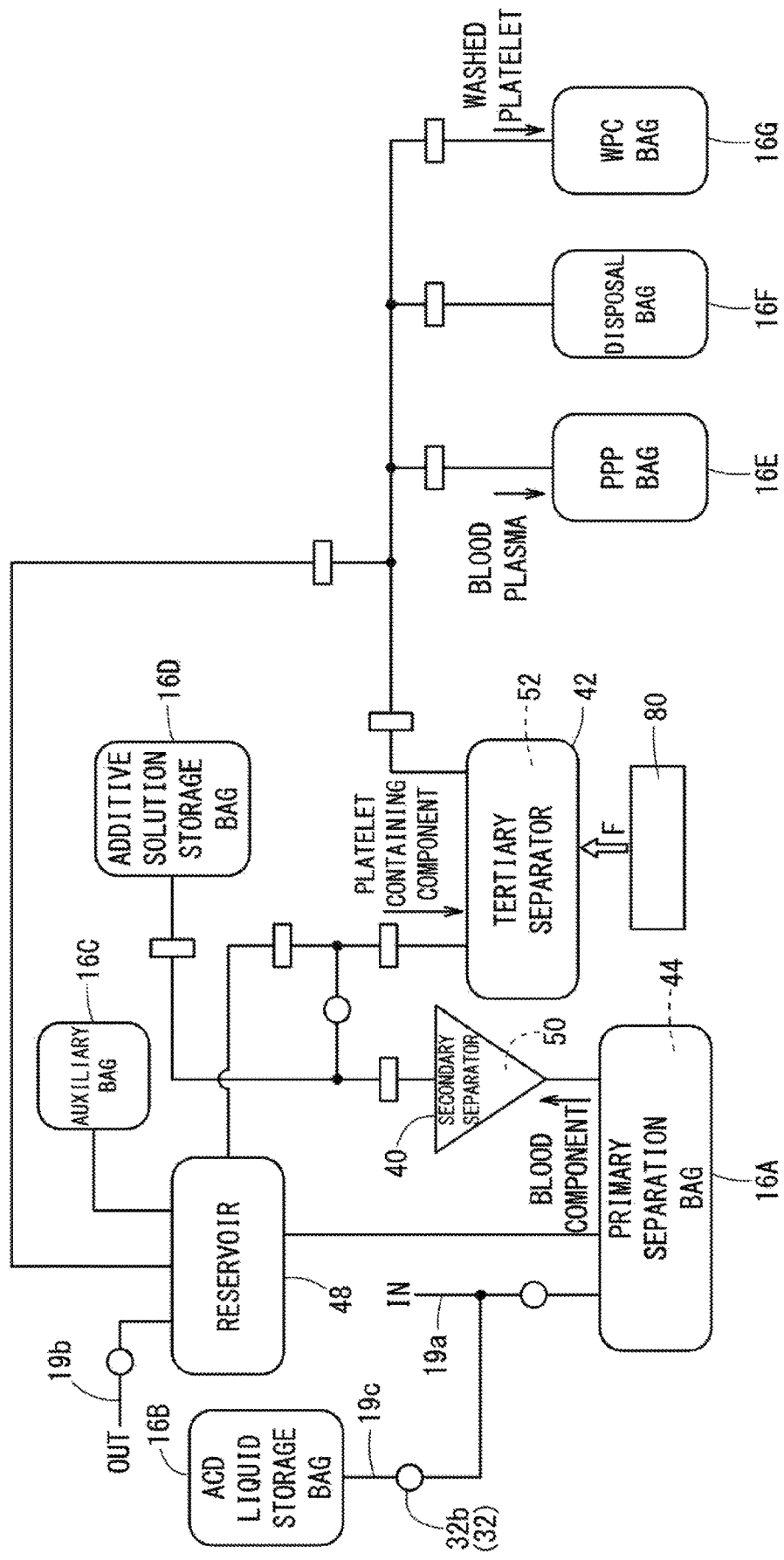
FIG. 11 is a block diagram schematically illustrating a circuit configuration example of a blood collection system according to a modification.

Even though the invention has been described above using a suitable embodiment, the invention is not limited to the embodiment, and various modifications may be made without departing from the spirit of the invention. For example, as in a collection system 10A according to a modification illustrated in FIG. 11 (a blood collection circuit set 12A), it is possible to adopt a configuration in which blood components other than concentrated red blood cells (components including the blood plasma, the platelet, and the white blood cell) are allowed to flow out to a secondary separator 40 from a primary separation bag 16A. In this case, a received blood component is centrifuged into a white blood cell and a platelet containing component 100 in the secondary separator 40, and the platelet containing component 100 is centrifuged into a platelet 104 and blood plasma 106 in a tertiary separator 42. Then, at a downstream side of the tertiary separator 42, first, the blood plasma 106 (platelet poor plasma) is stored in a PPP bag 16E. Thereafter, a platelet added solution 102 is supplied to the tertiary separator 42 to replace the blood plasma 106 with the platelet added solution 102 in a third chamber 52, and a washed platelet 108 containing reduced blood plasma 106 is stored in a WPC bag 16G together with the platelet added solution 102. When this configuration is adopted, it is possible to favorably collect the washed platelet 108 having a blood plasma content rate of 5% or less.

In the above description, a description has been given of a method of inhibiting the platelet 104 from being pelletized by supplying the external force F to the first bottom portion 60 using the external force supply unit 80 included in the centrifugal separator 14 during centrifugation treatment, and recovering the platelet 104 (washed platelet 108). However, instead of such a method, the platelet 104 may be recovered by removing the tertiary separator 42 from the centrifugal separator 14 after the centrifugation treatment and supplying an external force to the first bottom portion 60 without providing the external force supply unit 80 in the centrifugal separator 14 (or without using the external force supply unit 80 provided in the centrifugal separator 14).

In this case, for example, processes up to the above-described replacement process (step S7) are performed by the centrifugal separator 14, and the tertiary separator 42 in this state is removed together with the additive solution storage bag 16D and the WPC bag 16G from the centrifugal separator 14. In this instance, in the blood collection circuit set 12, components (bags, tubes) not necessary to recover the platelet 104 may be separated.

Figure 12:
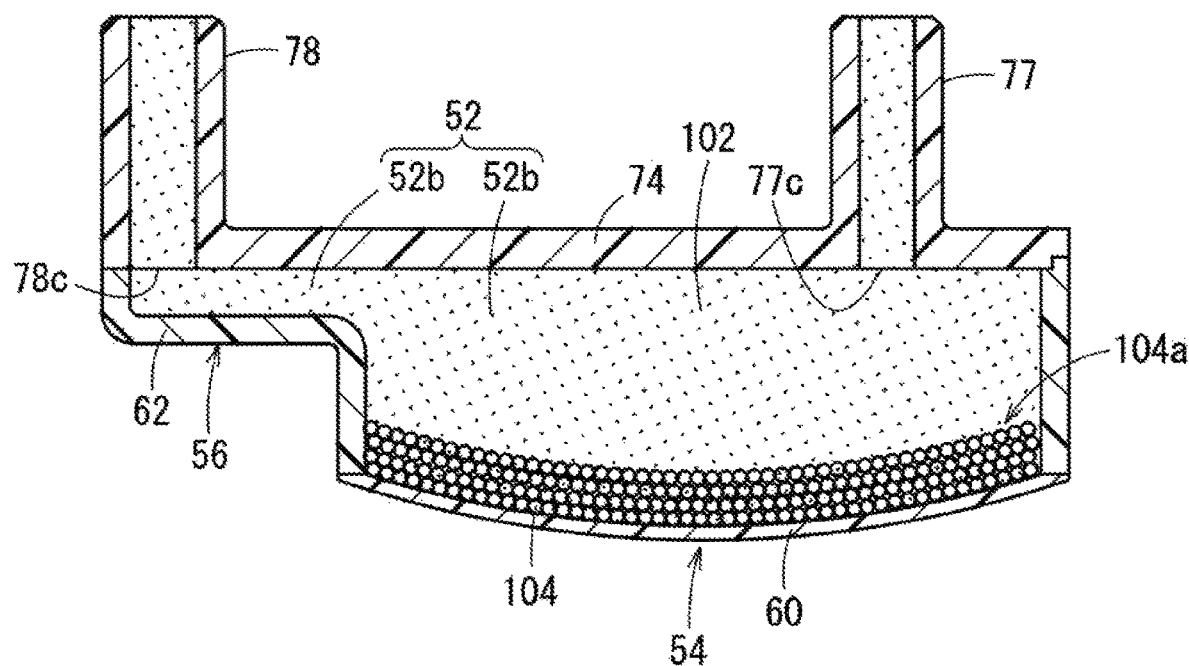
FIG. 12 is a cross-sectional view illustrating a state of the tertiary separator when a pelletized platelet is peeled off after a centrifugation treatment.

An external force is not supplied during centrifugation. Thus, as illustrated in FIG. 12, the tertiary separator 42 is filled with the platelet added solution 102, and the platelet 104 is pelletized therein (hereinafter the pelletized platelet 104 is denoted by "platelet 104a"). In this state, even when the platelet added solution 102 flows into the third chamber 52 at a high flow rate, since the pelletized platelet 104a sticks to the first bottom portion 60, it is difficult to peel off the pelletized platelet 104a. Therefore, the external force F is supplied to the first bottom portion 60 of the tertiary separator 42 using an appropriate external force supply device. Alternatively, the external force F is supplied to the first bottom portion 60 of the tertiary separator 42 by a manual operation (kneading, striking, and the like using a hand) of the operator. In this way, the pelletized platelet 104*a* may be peeled off from an inner surface of the main body 58.

Then, when the platelet 104 is peeled off from the inner surface inside the tertiary separator 42 (inside the third chamber 52) in this way, the platelet added solution 102 is discharged from the additive solution storage bag 16D and introduced to the tertiary separator 42. In this way, the platelet 104 is allowed to flow out from the tertiary separator 42 as the washed platelet 108 together with the platelet added solution 102, and the washed platelet 108 is recovered (collected) in the WPC bag 16G.

The same operation as that described above may be performed by separating the additive solution storage bag 16D from the tertiary separator 42 after the replacement process (step S7), and connecting another additive solution storage bag to the tertiary separator 42. Alternatively, after processes up to the replacement process (step S7) are performed using the blood collection circuit set 12 not provided with the WPC bag 16G from the beginning, the WPC bag may be connected to the tertiary separator 42, and the platelet added solution 102 may be introduced to the tertiary separator 42 from the additive solution storage bag 16D (or another additive solution storage bag described above).

Figure 13:
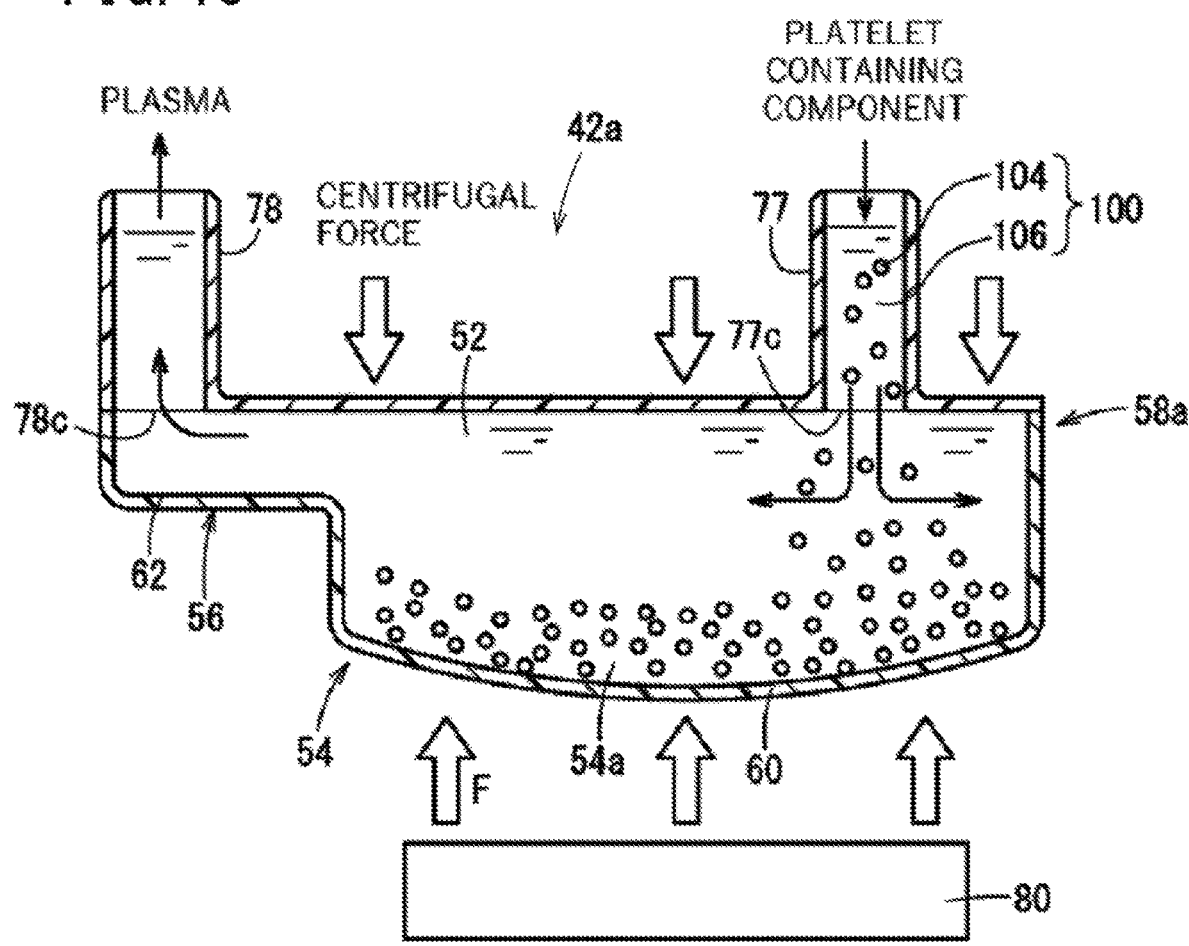
FIG. 13 is a cross-sectional view illustrating a state of a tertiary separator during a platelet separation process according to another embodiment.

In the above-described collection systems 10 and 10A, a tertiary separator 42*a* illustrated in FIG. 13 may be adopted instead of the tertiary separator 42. The tertiary separator 42*a* includes a main body 58*a* having a shape of a container which may store the platelet containing component 100 and the platelet added solution 102. The main body 58*a* is configured similarly to the main body 58 except that the whole body is formed of a soft material, and a wall thickness is thinner than that of the wall portion of the main body 58 (excluding the first bottom portion 60). Thus, the same reference symbol as that of the main body 58 is assigned to a corresponding component.

In the collection systems 10 and 10A, when the tertiary separator 42*a* configured as described above is adopted, the platelet 104 may be inhibited from being pelletized by supplying the external force F to the first bottom portion 60 during a centrifugation treatment of the tertiary separator 42*a* as illustrated in FIG. 13 using the external force supply unit 80 provided in the centrifugal separator 14. Therefore, it is possible to securely and efficiently recover the washed platelet 108 having a low blood plasma content rate. FIG. 13 representatively illustrates the platelet separation process (step S6). However, the replacement process (step S7) and the platelet collection process (step S8) may be performed in the same manner as in a case of the tertiary separator 42.

When the tertiary separator 42*a* configured as described above is adopted in the collection systems 10 and 10A, the tertiary separator 42*a* may be removed from the centrifugal separator 14 after the centrifugation treatment, and the platelet 104 may be recovered by supplying the external force F to the first bottom portion 60 without providing the external force supply unit 80 in the centrifugal separator 14 (or without using the external force supply unit 80 provided in the centrifugal separator 14).

Figure 14:
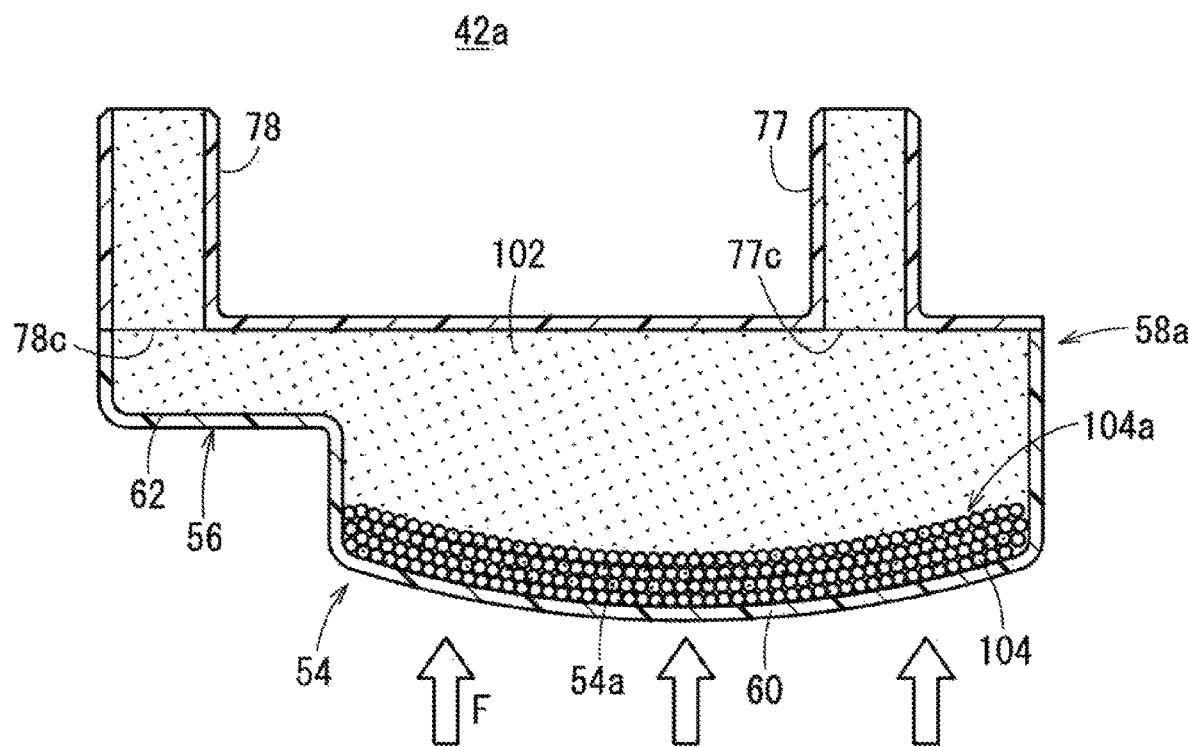
FIG. 14 is a cross-sectional view of the tertiary separator for description of another platelet collection method using the tertiary separator according to another embodiment.

That is, when processes up to the replacement process (step S7) described above are performed by the centrifugal separator 14, and the tertiary separator 42*a* in this state is removed from the centrifugal separator 14, the platelet 104 is pelletized in the third chamber 52 as illustrated in FIG. 14. Therefore, the external force F is supplied to the first bottom portion 60 of the tertiary separator 42*a* using an appropriate external force supply device. Alternatively, the external force F is supplied to the first bottom portion 60 of the tertiary separator 42*a* by a manual operation (kneading using a hand, and the like) of the operator. In this way, the pelletized platelet 104*a* may be peeled off from an inner surface of the main body 58*a*. A subsequent operation is the same as that in the case of the tertiary separator 42.

As described above, the tertiary separator 42*a* may inhibit the platelet 104 from being pelletized by supplying an external force during centrifugation treatment, and may peel off the pelletized platelet 104*a* by supplying an external force after the centrifugation treatment. In particular, according to the tertiary separator 42*a*, since the entire main body 58*a* is formed of a soft material, when the external force is supplied after the centrifugation treatment, the pelletized platelet 104*a* may be easily peeled off from the inner surface of the main body 58*a* by largely deforming the main body 58*a*.

REFERENCE SIGNS LIST

10, 10A collection system
12, 12A blood collection circuit set
14 centrifugal separator
16 bag
16A primary separation bag
18 tube
40 secondary separator
42, 42*a* tertiary separator
44 first chamber
50 second chamber
52 third chamber
54*a* accommodating portion
60 first bottom portion
62 second bottom portion
80 external force supply unit
100 platelet containing component
102 platelet added solution
108 washed platelet

The invention claimed is:
1. A disposable platelet recovery set comprising:
a primary separation unit adapted to be mounted on a rotor of a centrifuge, said primary separation unit comprising a flexible container having an inlet that accommodates whole blood collected from a donor to centrifuge the whole blood into at least a first blood component comprising platelets and a remaining fluid and at least one outlet;
a secondary separation unit adapted to be mounted on said rotor, said secondary separation unit comprising a rigid conical chamber for capturing white blood cells and having an inlet that accommodates the first blood component transferred from said outlet of the primary separation unit to centrifuge the first blood component into a platelet containing component and a white blood cell containing component and having an outlet; and
a tertiary separation unit adapted to be mounted on said rotor that centrifuges the platelet containing component transferred from the secondary separation unit, wherein the tertiary separation unit comprises
a chamber comprising
a ceiling,
a flexible bottom portion,
a first side wall connecting said ceiling and said flexible bottom portion, thereby forming a first region for receiving platelets and fluids, a second bottom portion spaced away from said first bottom portion,
a second side wall, said second side wall connecting said ceiling to said second bottom portion, forming a second region in fluid communication with said first region,
a step wall between said flexible bottom portion and said second bottom portion,
at least one inlet port in said ceiling in fluid communication with said first region and an outlet port in said ceiling in fluid communication with said second region.

2. The platelet recovery set according to claim 1, wherein the flexible bottom portion is thinner than the adjacent first side wall and step wall and wherein the chamber is formed of a soft material.

3. The chamber for separation platelets from fluids according to claim 1 wherein substantially all of said chamber is formed of a hard material except for said flexible bottom.

4. A chamber for separating platelets from fluids, said chamber being adapted to be mounted on a rotor of a centrifuge, wherein said chamber comprises
a ceiling,
a flexible bottom portion,
a first side wall connecting said ceiling and said flexible bottom portion, thereby forming a first region for receiving platelets and fluids,
a second bottom portion spaced away from said first bottom portion,
a second side wall, said second side wall connecting said ceiling to said second bottom portion, forming a second region in fluid communication with said first region,
a step wall between said flexible bottom portion and said second bottom portion,
at least one inlet port in said ceiling in fluid communication with said first region and an outlet port in said ceiling in fluid communication with said second region.
wherein the flexible bottom portion is thinner than the adjacent first side wall and step wall.

5. A chamber for separating platelets from fluids, said chamber being adapted to be mounted on a rotor of a centrifuge, wherein said chamber comprises
a ceiling,
a flexible bottom portion,
a first side wall connecting said ceiling and said flexible bottom portion, thereby forming a first region for receiving platelets and fluids,
a second bottom portion spaced away from said first bottom portion,
a second side wall, said second side wall connecting said ceiling to said second bottom portion, forming a second region in fluid communication with said first region,
a step wall between said flexible bottom portion and said second bottom portion,
at least one inlet port in said ceiling in fluid communication with said first region and an outlet port in said ceiling in fluid communication with said second region
wherein substantially all of said chamber is formed of a hard material except for said flexible bottom.

6. The chamber for separation platelets from fluids according to claim 5 wherein said ceiling is flat.

7. A platelet collection system comprising
a centrifuge having a rotor,
a disposable platelet recovery set comprising:
a primary separation unit adapted to be mounted on said rotor of said centrifuge, said primary separation unit comprising a flexible container having an inlet that receives whole blood collected from a donor to centrifuge the whole blood into at least a first blood component comprising platelets and a remaining fluid and at least one outlet;
a secondary separation unit adapted to be mounted on said rotor, said secondary separation unit comprising a rigid conical chamber for capturing white blood cells and having an inlet that receives the first blood component transferred from said outlet of the primary separation unit to centrifuge the first blood component into a platelet containing component and a white blood cell component and having an outlet; and
a tertiary separation unit adapted to be mounted on said rotor that centrifuges the platelet containing component transferred from the secondary separation unit, wherein the tertiary separation unit includes
a chamber comprising
a ceiling,
a flexible bottom portion,
a first side wall connecting said ceiling and said flexible bottom portion, thereby forming a first region for receiving platelets and fluids,
a second bottom portion spaced away from said flexible bottom portion,
a second side wall, said second side wall connecting said ceiling to said second bottom portion, forming a second region in fluid communication with said first region,
a step wall between said flexible bottom portion and said second bottom portion,
at least one inlet port in fluid communication with said first region and an outlet port in fluid communication with said second region,
and wherein said rotor further comprises an external force supply unit mechanically coupled to said flexible bottom portion of said chamber, said external force supply unit being radially outward from said chamber and imparting motion to said flexible bottom portion, thereby inhibiting settling of platelets against said flexible bottom portion.

8. The platelet collection system according to claim 7, wherein the flexible bottom portion is thinner than the adjacent first side wall and step wall and wherein the chamber is formed of a soft material.

9. The platelet collection system according to claim 7 wherein substantially all of said chamber is formed of a hard material except for said flexible bottom portion.

10. The platelet collection system according to claim 7 wherein the external force supplying unit comprises at least one of a vibrator, a striking device, or a finger pump.

11. A method for collecting platelets comprising
providing a quantity of whole blood,
separating said whole blood on a rotor of a centrifuge in a primary separation unit comprising a flexible container having an inlet that receives said whole blood into at least a first blood component comprising platelets and a remaining fluid;
removing white blood cells from said first blood component in a secondary separation unit comprising a rigid conical chamber thereby forming a second blood component; and
washing plasma from said second blood component in a tertiary separation unit adapted to be mounted on said rotor that centrifuges the platelet containing component transferred from the secondary separation unit, wherein the tertiary separation unit includes
a generally rectangular chamber comprising
a ceiling,
a first bottom portion, a first side wall connecting said ceiling and said first bottom portion, thereby forming a first region for receiving platelets and fluids, a second bottom portion spaced away from said first bottom portion, a second side wall, said second side wall connecting said ceiling to said second bottom portion, forming a second region in fluid communication with said first region, a step wall between said first bottom portion and said second bottom portion, at least one inlet port in said ceiling in fluid communication with said first region and an outlet port in fluid communication with said second region, wherein said washing step comprises
  settling platelets in said first region,
  flushing plasma out of said first region through said second region into said outlet port, and
  replacing said plasma with another fluid.

12. The method for collecting platelets according to claim 11, further comprising
  providing a flexible diaphragm at said first bottom portion and
  agitating said diaphragm with an external force supply unit mounted on said rotor while said generally rectangular chamber is on said rotor to inhibit platelets from being pelletized in said chamber.

13. The method for collecting platelets according to claim 11, further comprising
  a flexible diaphragm at said first bottom portion and
  agitating said diaphragm after said tertiary separation unit has been removed from said rotor to inhibit platelets from being pelletized in said chamber.

* * * * *